US012595236B2

(12) United States Patent
Liu et al.

(10) Patent No.: US 12,595,236 B2
(45) Date of Patent: Apr. 7, 2026

(54) PYRIMIDINE-2,4-DIAMINE COMPOUND AND PREPARATION METHOD AND APPLICATION THEREOF

(71) Applicant: ANHUI MEDICAL UNIVERSITY, Hefei (CN)

(72) Inventors: Xinhua Liu, Hefei (CN); Xing Chen, Hefei (CN); Jingbo Shi, Hefei (CN); Mingming Liu, Hefei (CN); Yaoyao Yan, Hefei (CN); Zhaoyan Zhang, Hefei (CN); Famin Zhang, Hefei (CN)

(73) Assignee: ANHUI MEDICAL UNIVERSITY, Hefei (CN)

(*) Notice: Subject to any disclaimer, the term of this patent is extended or adjusted under 35 U.S.C. 154(b) by 743 days.

(21) Appl. No.: 17/915,121

(22) PCT Filed: Jan. 21, 2022

(86) PCT No.: PCT/CN2022/073177
§ 371 (c)(1),
(2) Date: Sep. 28, 2022

(87) PCT Pub. No.: WO2022/161274
PCT Pub. Date: Aug. 4, 2022

(65) Prior Publication Data

US 2023/0150947 A1 May 18, 2023

(30) Foreign Application Priority Data

Jan. 29, 2021 (CN) ......................... 202110129457.2

(51) Int. Cl.

| | |
|---|---|
| ***C07D 239/48*** | (2006.01) |
| ***A61P 11/00*** | (2006.01) |
| ***A61P 29/00*** | (2006.01) |
| ***C07D 401/12*** | (2006.01) |
| ***C07D 401/14*** | (2006.01) |
| ***C07D 403/12*** | (2006.01) |
| ***C07D 405/14*** | (2006.01) |
| ***C07D 409/14*** | (2006.01) |
| ***C07D 413/14*** | (2006.01) |

(52) U.S. Cl.
CPC ............ *C07D 239/48* (2013.01); *A61P 11/00* (2018.01); *A61P 29/00* (2018.01); *C07D 401/12* (2013.01); *C07D 401/14* (2013.01); *C07D 403/12* (2013.01); *C07D 405/14* (2013.01); *C07D 409/14* (2013.01); *C07D 413/14* (2013.01)

(58) Field of Classification Search
CPC .. C07D 239/48; C07D 401/12; C07D 401/14; C07D 403/12; C07D 405/14; C07D 409/14; C07D 413/14
See application file for complete search history.

(56) References Cited

U.S. PATENT DOCUMENTS

2011/0212077 A1* 9/2011 Noronha ............ A61K 31/4545
544/323

FOREIGN PATENT DOCUMENTS

| | | | | |
|---|---|---|---|---|
| CN | 1625400 A | | 6/2005 | |
| CN | 1678321 A | | 10/2005 | |
| CN | 101370792 A | | 2/2009 | |
| CN | 105017159 A | * | 11/2015 | ........... C07D 239/42 |
| CN | 105017160 A | * | 11/2015 | ........... C07D 239/48 |
| CN | 111620852 A | | 9/2020 | |
| CN | 112920124 A | | 6/2021 | |
| WO | WO-2008106635 A1 | * | 9/2008 | ................ A61P 3/10 |
| WO | WO-2016033100 A1 | * | 3/2016 | ........... A61K 31/505 |
| WO | WO-2018019252 A1 | * | 2/2018 | ........... C07D 401/14 |

OTHER PUBLICATIONS

Calder, P. C.; et al. "Inflammatory Disease Processes and Interactions with Nutrition", British Journal of Nutrition 2009, vol. 101(S1), pp. 1-45. (Year: 2009).*
Merriam Webster Dictionary definition of "aliphatic" (accessed May 28, 2025). (Year: 2025).*
Wang, Y. et al. "Discovery and SARs of 5-Chloro-N4-phenyl-N2-(pyridin-2-yl)pyrimidine-2,4-diamine Derivatives as Oral Available and Dual CDK 6 and 9 Inhibitors with Potent Antitumor Activity", Journal of Medicinal Chemistry 2021, vol. 64, pp. 11857-11885. (Year: 2021).*
English language machine translation of CN105017159A; translated May 27, 2025. (Year: 2015).*
English language machine translation of CN105017160A; translated May 27, 2025. (Year: 2015).*
Beingessner, R. L.; et al. "A Regioselective Approach to Trisubstituted 2 (or 6)-Arylaminopyrimidine-5-carbaldehydes and Their Application in the Synthesis of Structurally and Electronically Unique GˆC Base Precursors", Journal of Organic Chemistry 2008, vol. 73, pp. 931-939. (Year: 2008).*
Park, C. L.; et al. "1-(Arylsulfonyl)-2,3-dihydro-1H-quinolin-4-one derivatives as 5-HT6 serotonin receptor ligands", Bioorganic and Medicinal Chemistry Letters 2011, vol. 21, pp. 698-703. (Year: 2011).*

(Continued)

*Primary Examiner* — Andrea Olson
*Assistant Examiner* — Benjamin M Brandsen
(74) *Attorney, Agent, or Firm* — Bayramoglu Law Offices LLC

(57) ABSTRACT

A pyrimidine-2,4-diamine compound and a preparation method and application thereof are provided. The pyrimidine-2,4-diamine compound of the present disclosure can be used in the research of biological or pharmacological phenomena and cathepsin C-involved signal pathway transduction and the evaluation of novel cathepsin C inhibitors. The pyrimidine-2,4-diamine compound is subjected to the screening of anti-cathepsin C activity in vitro and in vivo and proved to have strong inhibitory activity on cathepsin C. The pyrimidine-2,4-diamine compound is subjected to the screening of anti-NSP activity in vivo and proved to have strong inhibitory activity on NSP. The pyrimidine-2,4-diamine compound is subjected to the screening of anti-inflammatory activity in vivo and proved to have an effective therapeutic effect on inflammatory disease models. Meanwhile, the pyrimidine-2,4-diamine compound shows low toxicity and exhibits good application prospect.

2 Claims, 3 Drawing Sheets

(56) References Cited

OTHER PUBLICATIONS

Yi, Y.-S.; et al. "Functional Roles of Syk in Macrophage-Mediated Inflammatory Responses", Mediators of Inflammation 2014, Article ID 270302. (Year: 2014).*

Chen, "Design, Synthesis, Activity, Evaluation and Structure-activity Relationship of Small Molecule Inhibitors Targeting CDK6", Master's Thesis, Anhui Medical University, 2019. (Year: 2019).*

English language translation of: Chen, "Design, Synthesis, Activity, Evaluation and Structure-activity Relationship of Small Molecule Inhibitors Targeting CDK6", Master's Thesis, Anhui Medical University, 2019. (Year: 2019).*

Wang, Y. et al. "Discovery and SARs of 5-Chloro-N4-phenyl-N2-(pyridin-2-yl)pyrimidine-2,4-diamine Derivatives as Oral Available and Dual CDK 6 and 9 Inhibitors with Potent Antitumor Activity", Journal of Medicinal Chemistry 2020, vol. 63, pp. 3327-3347. (Year : 2020).*

Korkmaz, B.; et al. "Therapeutic targeting of cathepsin C: from pathophysiology to treatment", Pharmacology and Therapeutics 2018, vol. 190, pp. 202-236. (Year: 2018).*

Adkison, A. M.; et al. "Dipeptidyl peptidase I activates neutrophil-derived serine proteases and regulates the development of acute experimental arthritis", The Journal of Clinical Investigation 2002, vol. 109, pp. 363-371. (Year: 2002).*

Mallen-St. Clair, J.; et al. "Mast cell dipeptidyl peptidase I mediates survival from sepsis", The Journal of Clinical Investigation 2004, vol. 113, pp. 628-634. (Year: 2004).*

Pagano, M. B.; et al. "Critical role of dipeptidyl peptidase I in neutrophil recruitment during the development of experimental abdominal aortic aneurysms", Proceedings of the National Academy of Sciences 2007, vol. 104, pp., 2855-2860. (Year: 2007).*

Xing Chen, et al., Discovery and In Vivo Anti-inflammatory Activity Evaluation of a Novel Non-peptidyl Non-covalent Cathepsin C Inhibitor, Journal of Medicinal Chemistry, 2021, pp. A-AC.

Zhang Ying, et al., The synthesis and antitumor activities and molecular docking of novel pyrimidine EGFRT790M inhibitors, Chinese Journal of Medicinal Chemistry, 2015, pp. 269-274, vol. 25, No. 4.

* cited by examiner

PYRIMIDINE-2,4-DIAMINE COMPOUND AND PREPARATION METHOD AND APPLICATION THEREOF

CROSS REFERENCE TO THE RELATED APPLICATIONS

This application is the national phase entry of International Application No. PCT/CN2022/073177, filed on Jan. 21, 2022, which is based upon and claims priority to Chinese Patent Application No. 202110129457.2, filed on Jan. 29, 2021, the entire contents of which are incorporated herein by reference.

TECHNICAL FIELD

The present disclosure relates to the technical field of medicinal chemistry, in particular to a pyrimidine-2,4-diamine compound and a preparation method and application thereof.

BACKGROUND

The development of drugs for treating inflammatory and autoimmune diseases has always been an important pursuit in the field of medicinal chemistry. A great many drugs have been widely used in clinical treatment but show undesirable safety. Therefore, in the current stage, drug safety is the foremost factor during the development of new anti-inflammatory drugs and drugs for treatment of autoimmune diseases.

Severe acute respiratory syndrome coronavirus 2 (SARS-CoV-2) has been rampant worldwide. A patient with a severe inflammatory disease who is infected with SARS-CoV-2 cannot tolerate side effects of a traditional anti-inflammatory drug. As a result, finding novel, effective and safe therapeutic targets and developing corresponding drugs is a demand for the treatment of inflammatory and autoimmune diseases, which is even more urgent for the treatment of severe inflammatory diseases with SARS-CoV-2 infection.

Seeking novel, effective and safe therapeutic targets is the basic starting point to achieve breakthrough. Cathepsin C, also known as dipeptidyl peptidase 1 (DPP1, CTSC, EC 3.4.14.1), is an important lysosomal cysteine protease and derives from the papain family. Cathepsin C is involved in polymorphonuclear neutrophil-related inflammation and immune regulation by mediating the maturation of neutrophil serine protease (NSP). Therefore, cathepsin C is an effective target for the treatment of inflammatory and autoimmune diseases.

Polymorphonuclear neutrophils are the cells that are first recruited to the site of inflammation and form the first line of defense against invading microorganisms. One of the mechanisms by which polymorphonuclear neutrophils exert their immune functions is that the polymorphonuclear neutrophils can secrete NSP, including elastase (NE), cathepsin G, protease 3 (PR3), and NSP4. Early in neutrophil maturation, NSPs are synthesized in the form of inert zymogen that contains a dipeptide structure at the amino terminus. After NSP zymogens are activated by cathepsin C, mature NSPs bind to reactive oxygen species produced by a complex of myeloperoxidase and nicotinamide adenine dinucleotide phosphate (NADPH) oxidase to facilitate degradation of pathogenic microorganisms in phagolysosome. In certain disease states, excessive secretion of active NSPs caused by accumulation and activation of neutrophils may lead to tissue damage and inflammation. NSPs are involved in the progress of various inflammatory diseases, such as sepsis, acute pancreatitis, rheumatoid arthritis, anti-neutrophil cytoplasmic antibody-associated necrotizing crescentic glomerulonephritis, chronic obstructive pulmonary disease (COPD), bronchiectasis, and cystic fibrosis. Furthermore, recent evidences suggest that the extracellular secretion of NSPs may lead to the formation of neutrophil extracellular traps, which is considered as a driver of severe coronavirus disease 2019 (COVID-19). Therefore, NSPs are considered as promising biological targets for the treatment of neutrophil-related inflammatory diseases including COVID-19. Cathepsin C is involved in regulating inflammatory and immune processes by mediating the maturation of NSPs. Therefore, drugs that exert anti-inflammatory effects by targeting cathepsin C must be able to affect the activity of NSPs in vivo.

The development of cathepsin C inhibitors has been lasting for more than three decades. It was not until June 2020 that the U.S. Food and Drug Administration approved the cathepsin C inhibitor brensocatib which had just completed the phase II clinical trial as a breakthrough therapy designated drug for treating adults with non-cystic fibrosis bronchiectasis (NCFBE).

Almost all reported cathepsin C inhibitors contain a "warhead" capable of forming a covalent bond with Cys234. Electrophilic "warhead" generally can improve target selectivity and efficiency. However, peptide and electrophilic properties of these cathepsin C inhibitors sometimes are associated with poor metabolic stability. The high reactivity of electrophilic "warhead" sometimes may lead to poor selectivity and off-target effects, probably posing potential safety hazards. These problems severely hinder drug development and may also be the main cause of slow progress of cathepsin C inhibitors in clinical drug development.

Since cathepsin C inhibitor/substrate binding environment is relatively shallow, it is generally believed that non-covalent inhibitors have limited interaction and are not suitable for being developed as small-molecule cathepsin C inhibitors. We disagree with this opinion because we believe that non-covalent inhibitors can also effectively inhibit the catalytic activity of cathepsin C. Although Cys234 is the critical amino acid for realizing functions of cathepsin C, there is no evidence showing the necessity of introducing an electrophilic "warhead" during the development of potent cathepsin C inhibitors. Poor metabolic stability and potential safety hazards caused by electrophilic "warhead" must be overcome. Therefore, we decide to develop a novel "non-peptide derivative non-covalent cathepsin C inhibitor" to inhibit the activity of cathepsin C and the activation of downstream NSPs and to exhibit potent in vivo anti-inflammatory activity while avoiding the poor metabolic stability and the potential safety hazards caused by electrophilic "warhead". To date, there are no reports of small molecules acting as "non-peptide derivative non-covalent cathepsin C inhibitors" to inhibit cathepsin C and downstream NSP activation.

In the present disclosure, the research and development of "non-peptide derivative non-covalent cathepsin C inhibitor" is conducted using pyrimidine-2,4-diamine as a core structural skeleton, which is determined through the screening of compound molecular library and structure-based medicinal chemistry optimization. In this way, it is expected to discover cathepsin C inhibitors with better therapeutic effects and expand the library of small molecules targeting cathepsin C.

SUMMARY

The technical problem to be solved by the present disclosure is to provide a pyrimidine-2,4-diamine compound and a preparation method thereof. The pyrimidine-2,4-diamine compound, as a "non-peptide derivative non-covalent cathepsin C inhibitor", can be used in the preparation of a drug for preventing or treating inflammatory and autoimmune diseases.

The technical problem to be solved by the present disclosure is solved by using the following technical solution:

A pyrimidine-2,4-diamine compound, as shown in Formula I and Formula II:

Formula I

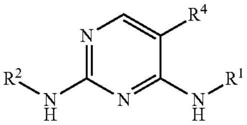

Formula II

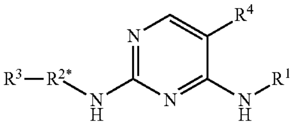

where, $R^1$ is selected from phenyl or substituted phenyl;

$R^2$ is any one selected from aliphatic group, phenyl, substituted phenyl, benzyl, substituted benzyl, phenethyl, substituted phenethyl, pyridyl, pyrimidinyl, and pyridazinyl;

$R^{2*}$ is any one selected from phenyl, pyridyl, pyrimidinyl, and pyridazinyl;

$R^3$ is any one selected from N-methylpiperazine, N-ethylpiperazine, N-propylpiperazine, N-cyclopropylpiperazine, N-butylpiperazine, N-acetylpiperazine, N-propionylpiperazine, piperazine, piperidine, morpholine, thiomorpholine, 4-aminopiperidine, 4-dimethylaminopiperidine, 4-cyanopiperidine, phenyl, substituted phenyl, furyl, substituted furan, thienyl, substituted thienyl, isoxazolyl, substituted isoxazolyl, pyrazolyl, and substituted pyrazolyl;

$R^4$ is any one selected from hydrogen, fluorine, chlorine, bromine, methyl, ethyl, and methoxy.

The pyrimidine-2,4-diamine compound has structural formulas shown below (compound 1-71):

1

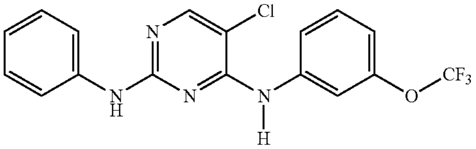

2

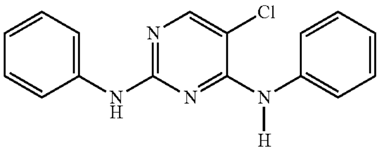

3

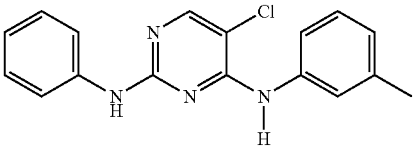

-continued

4

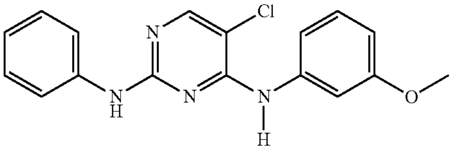

5

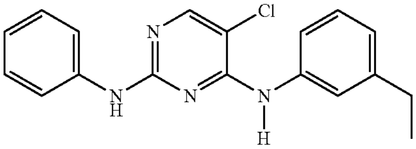

6

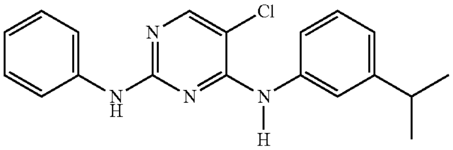

7

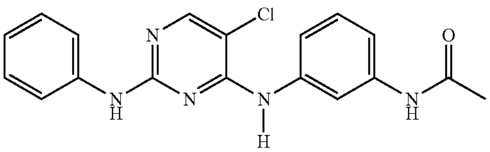

8

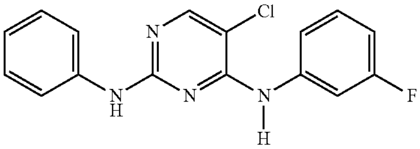

9

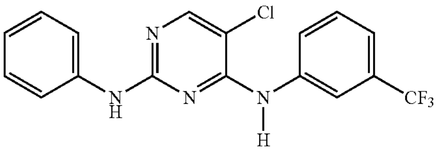

10

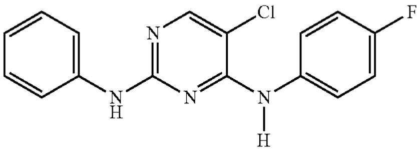

11

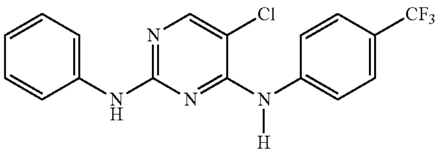

12

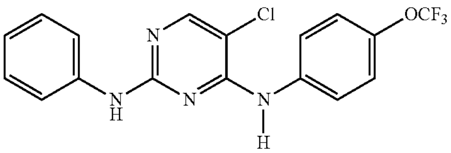

13

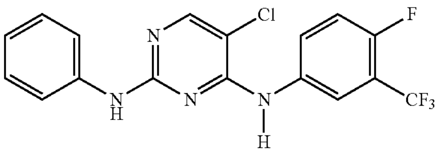

-continued
14
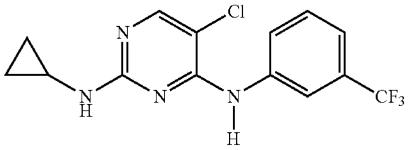
15
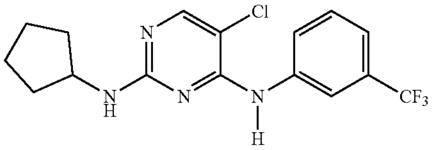
16
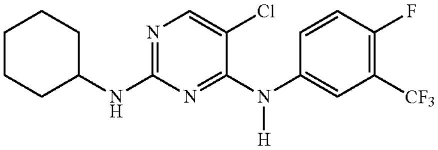
17
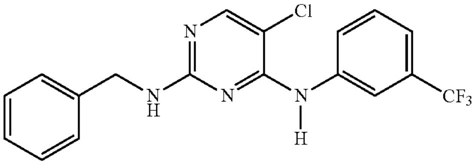
18
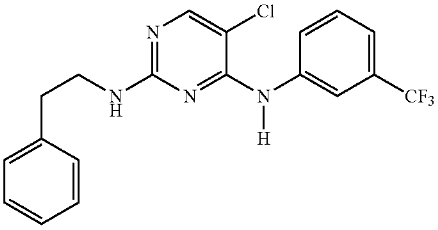
19
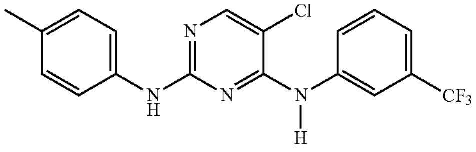
20
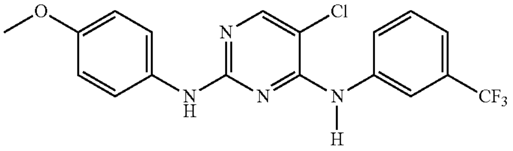
21
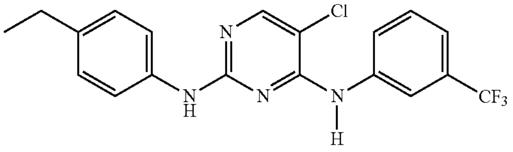
-continued
22
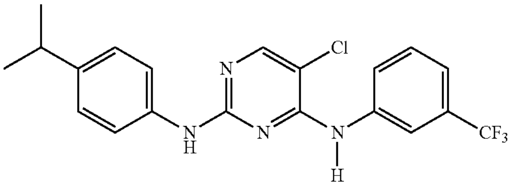
23
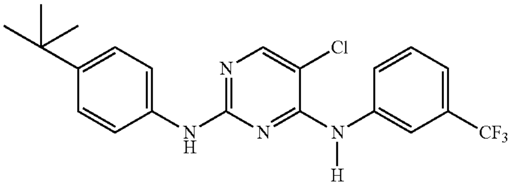
24
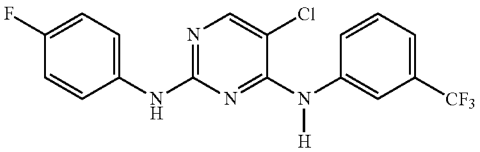
25
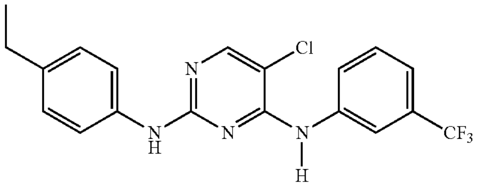
26
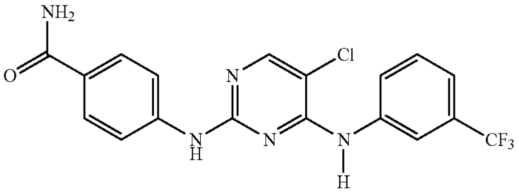
27
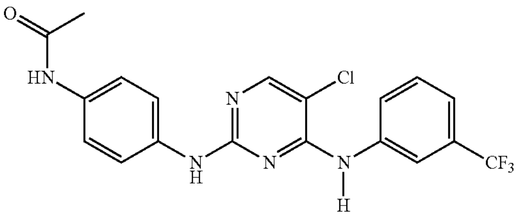
28
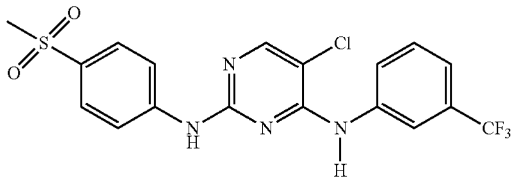

-continued
29
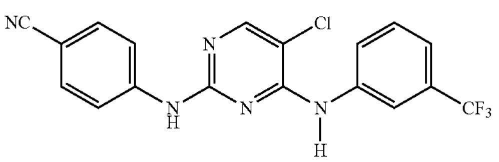
30
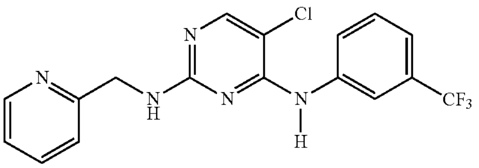
31
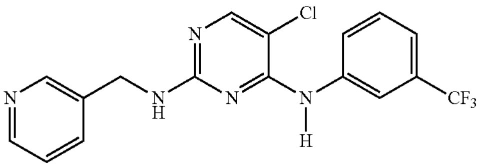
32
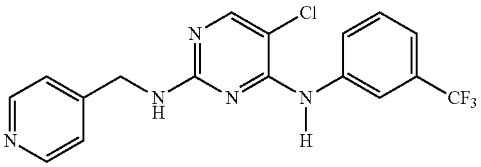
33
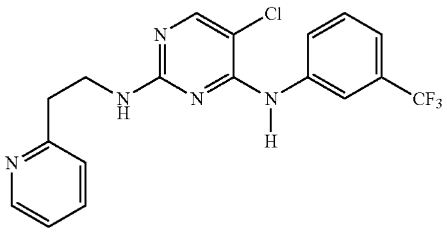
34
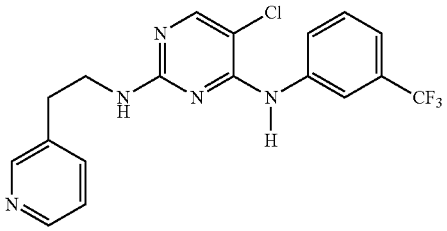
35
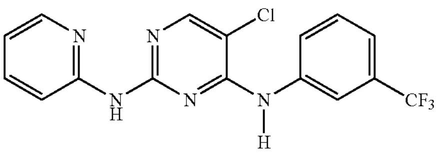
36
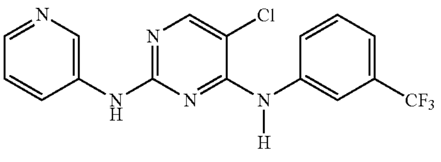
-continued
37
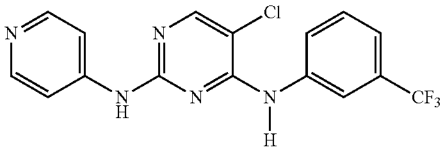
38
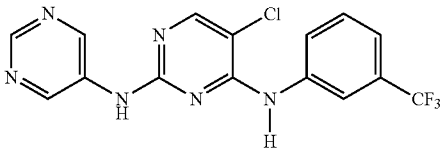
39
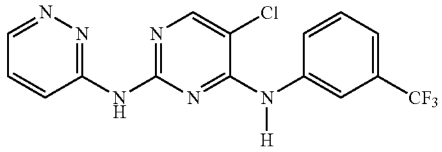
40
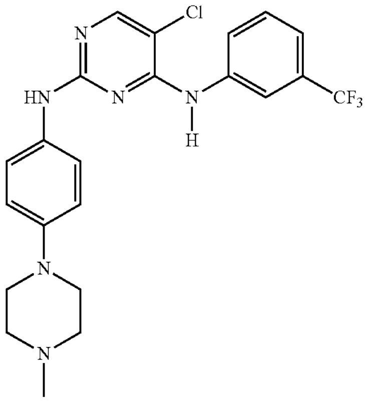
41
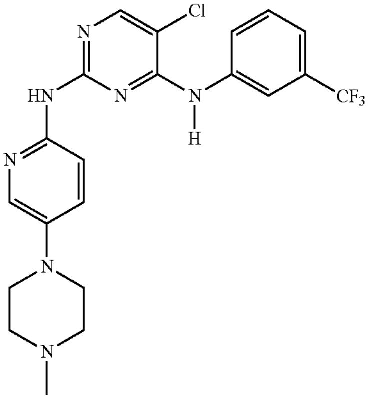

-continued
42
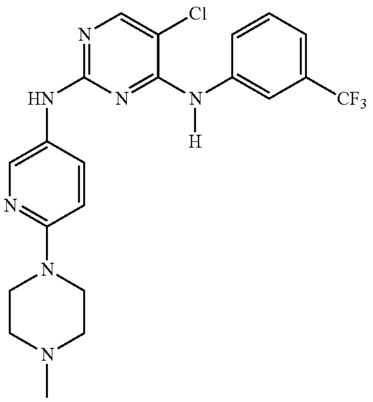
43
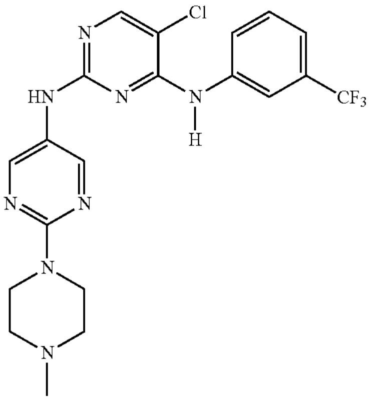
44
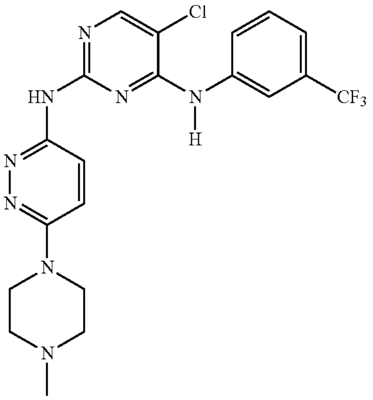
45
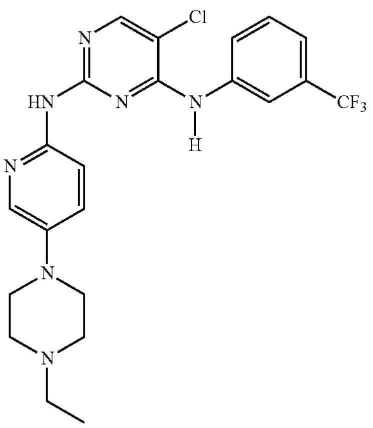
-continued
46
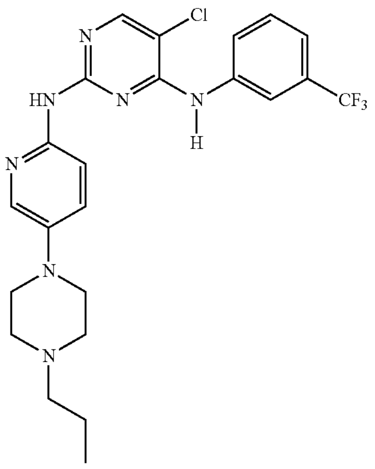
47
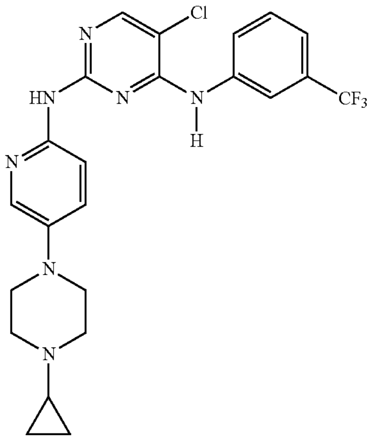
48
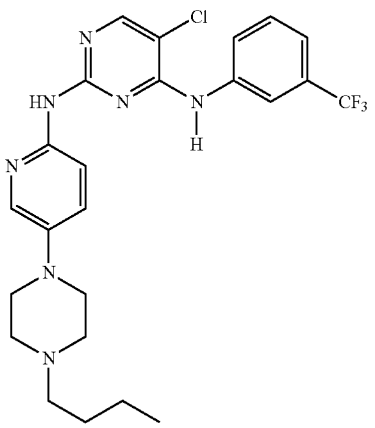

-continued
49
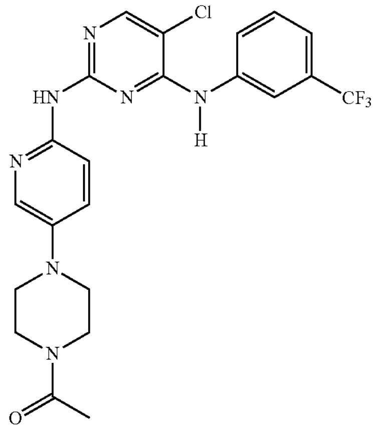
50
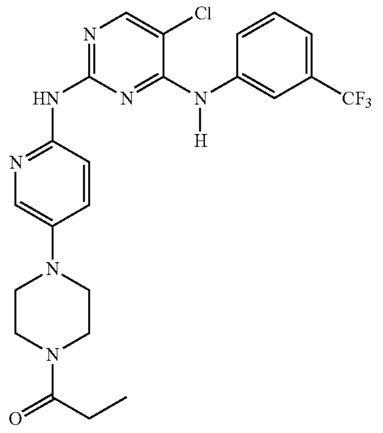
51
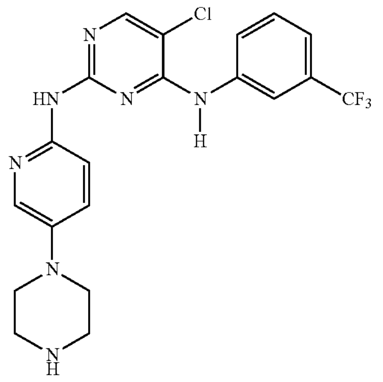
52
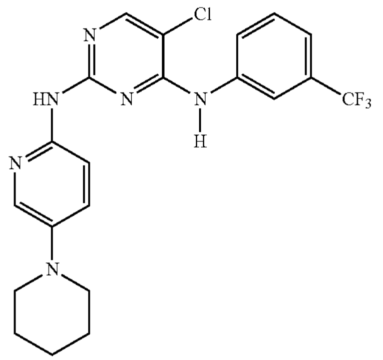
-continued
53
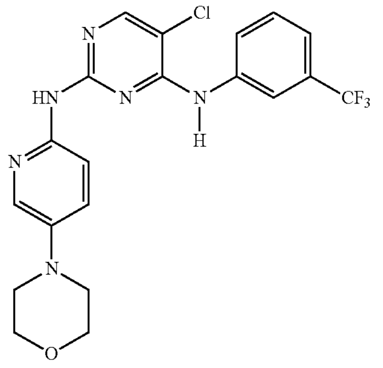
54
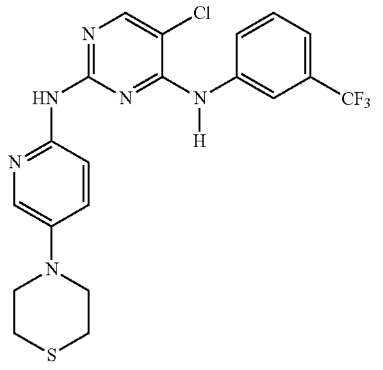
55
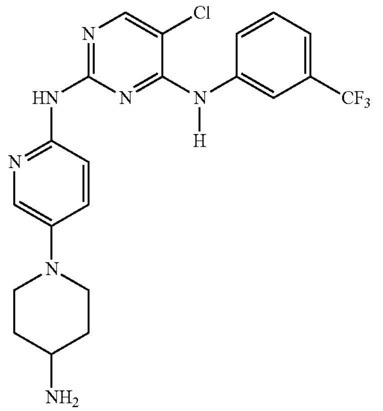
56
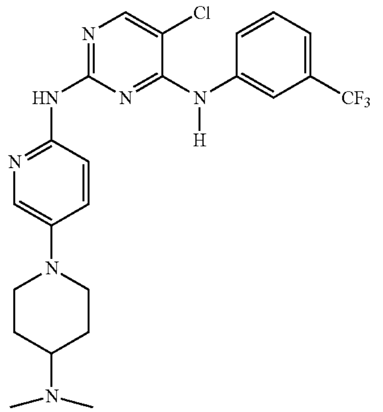

-continued
57
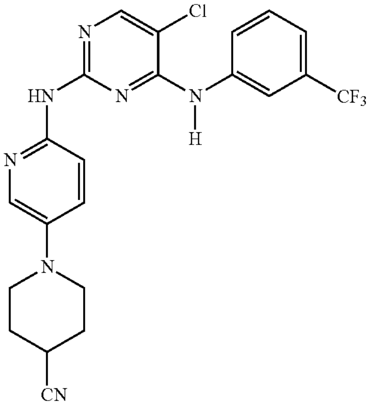
58
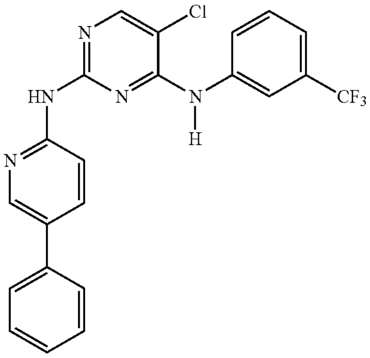
59
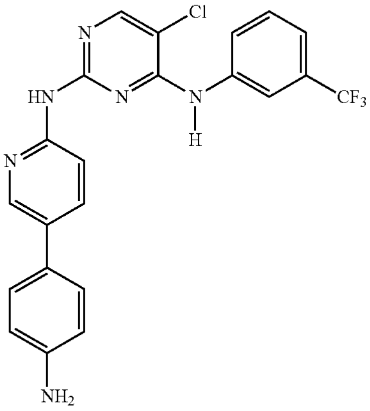
60
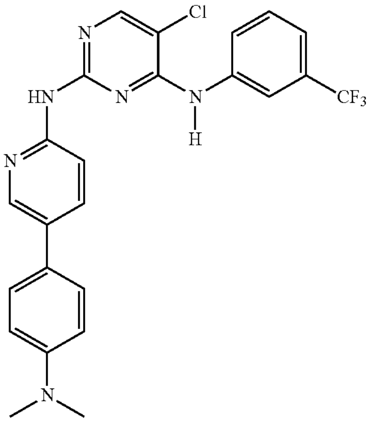
-continued
61
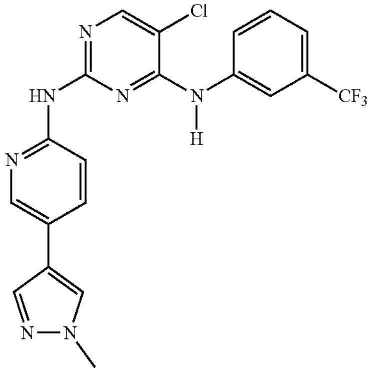
62
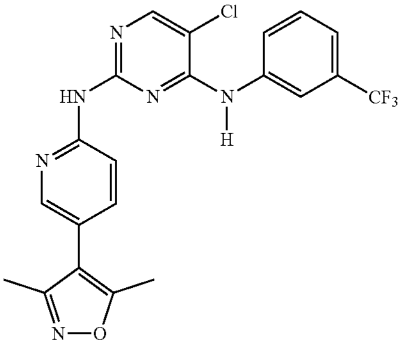
63
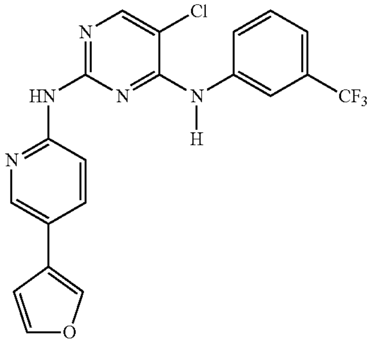
64
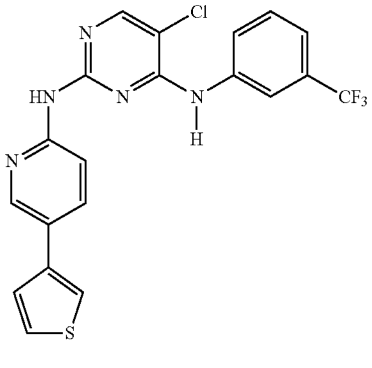

-continued

65

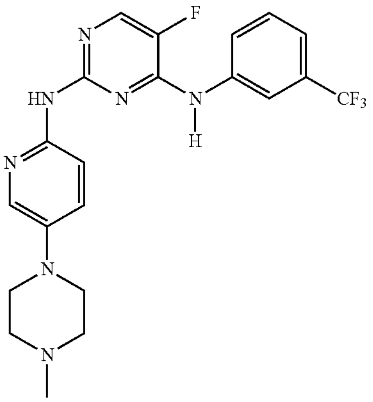

66

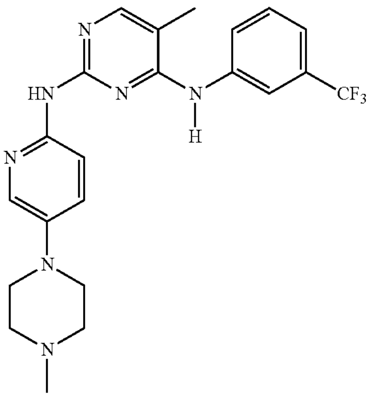

67

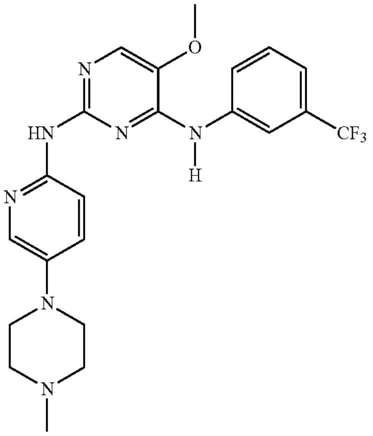

68

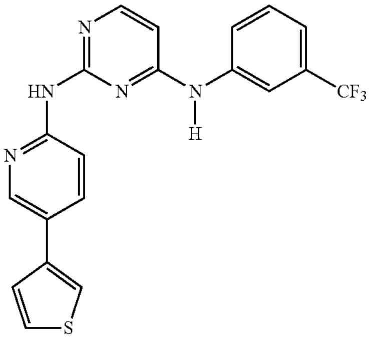

-continued

69

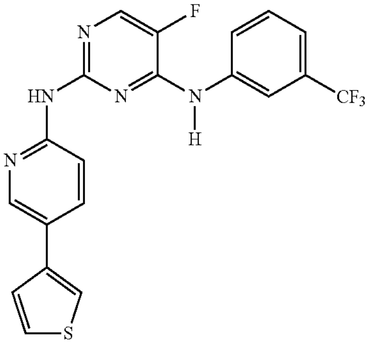

70

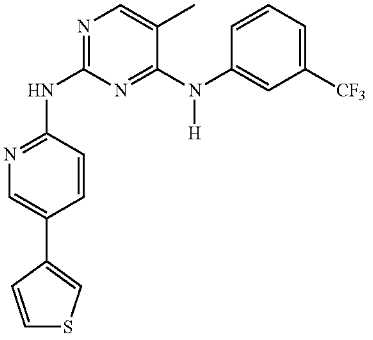

71

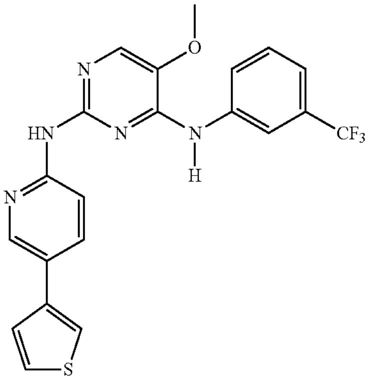

A preparation method of the pyrimidine-2,4-diamine compound, including the following steps:

(1) subjecting a 2,4-dichloropyrimidine or C5-substituted 2,4-dichloropyrimidine compound and $R^1$—$NH_2$ to a nucleophilic substitution reaction under the catalysis of tetrabutylammonium iodide to obtain an intermediate I;

(2) subjecting the intermediate I and $R^2$—$NH_2$ to a Buchwald-Hartwig reaction to obtain the pyrimidine-2,4-diamine compound shown in Formula I;

(3) subjecting the compound $NO_2$—$R^{2*}$—Br and heterocyclic amine or aniline or substituted aniline to a nucleophilic substitution reaction to obtain an intermediate II;

(4) subjecting the intermediate II to a hydrogenation to obtain an intermediate III;

(5) subjecting the intermediate I and the intermediate III to a Buchwald-Hartwig reaction to obtain the pyrimidine-2,4-diamine compound shown in Formula II.

The reaction equation is as follows:

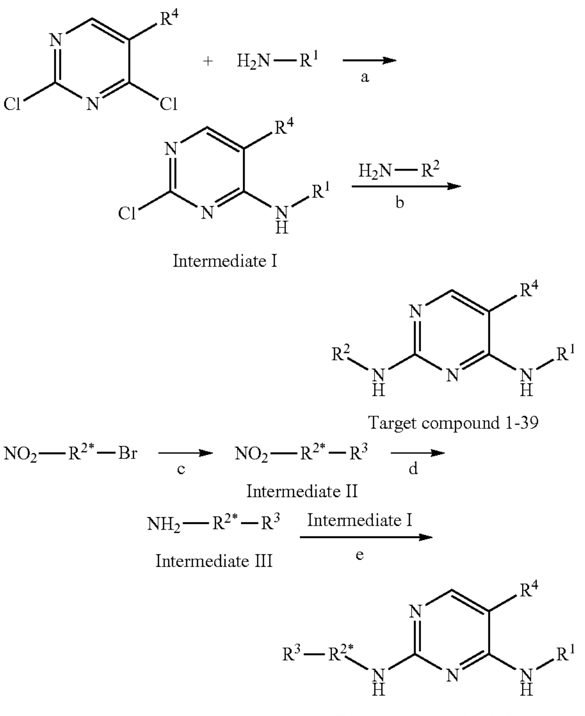

Target compounds 40-71

An application of the pyrimidine-2,4-diamine compound in the preparation of a preparation for regulating the catalytic activity of cathepsin.

Further, the cathepsin is cathepsin C.

An application of the pyrimidine-2,4-diamine compound in the preparation of a drug for treating inflammatory and autoimmune diseases.

Further, the inflammatory and autoimmune diseases are selected from arthritis, rheumatoid arthritis, sepsis, acute pancreatitis, nephritis, COPD, cystic fibrosis, and bronchiectasis.

The present disclosure has the following advantages:

(1) The pyrimidine-2,4-diamine compound of the present disclosure can be used in the research of biological or pharmacological phenomena and cathepsin C-involved signal pathway transduction and the evaluation of novel cathepsin C inhibitors;

(2) The pyrimidine-2,4-diamine compound of the present disclosure is subjected to the screening of anti-cathepsin C activity in vitro and proved to concurrently have strong inhibitory activity on cathepsin C and low toxicity;

(3) The pyrimidine-2,4-diamine compound of the present disclosure is subjected to the screening of anti-cathepsin C activity in vivo and proved to concurrently have strong inhibitory activity on cathepsin C and low toxicity;

(4) The pyrimidine-2,4-diamine compound of the present disclosure is subjected to the screening of anti-NSP activity in vivo and proved to concurrently have strong inhibitory activity on NSP and low toxicity;

(5) The pyrimidine-2,4-diamine compound of the present disclosure is subjected to the screening of anti-inflammatory activity in vivo and proved to concurrently have an effective therapeutic effect on inflammatory disease models and low toxicity;

(6) The pyrimidine-2,4-diamine compound of the present disclosure has new structure, involves simple synthesis process, possesses high product purity, and shows good application prospect.

DETAILED DESCRIPTION OF THE EMBODIMENTS

Figure 1A:
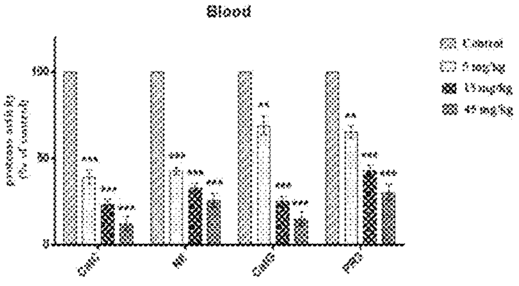
FIGS. 1A-1B show inhibitory effects of compound 41 of the present disclosure on cathepsin C and downstream NSPs in normal mice.

In order to make the technical means, creative features, and purposes and effects to be achieved of the present disclosure easily understand, the present disclosure is further described below with reference to specific embodiments and drawings.

Embodiment 1

Synthesis of Compound 41

5-chloro-$N^2$-(5-(4-methylpiperazin-1-yl)pyridin-2-yl)-$N^4$-(3-(trifluoromethyl)phenyl)pyrimidine-2,4-diamine

1.1 Preparation of Intermediate I-1: 2,5-dichloro-N-(3-(trifluoromethyl)phenyl)pyrimidin-4-amine 0.5 g (2.73 mmol) of 2,4,5-trichloropyrimidine was weighed and added into a 50 mL round-bottomed flask, followed by dissolving with 5 mL of dimethyl sulfoxide, adding a catalytic amount of tetrabutylammonium iodide, and stirring for 5 min. After the resulting solution changed from colorless to yellow, 0.28 g (3.00 mmol) of m-trifluoromethylaniline and 0.3 g (3.00 mmol) of triethylamine were added and stirred at room temperature for 3 h. The reaction endpoint was detected by thin layer chromatography (petroleum ether:ethyl acetate=20:1). After the reaction was ended, the reaction was quenched with 25 mL of ice water. The resulting mixture was stirred for 30 min and extracted with ethyl acetate (three times, 30 mL each time). The extracted ethyl acetate layers were combined and washed three times with saturated sodium chloride solution. The washed ethyl acetate layer was dried with anhydrous sodium sulfate for 24 h, filtered, and concentrated. The obtained residue was purified and separated by an automated medium pressure chromatography system. The product was a white solid with a yield of 89% (0.58 g). White solid (yield 89%). mp 121-122° C.; $^1$H NMR (600 MHz, Chloroform-d) δ 8.26 (s, 1H), 7.91 (d, J=8.2 Hz, 1H), 7.88 (s, 1H), 7.54 (t, J=8.0 Hz, 1H), 7.45 (d, J=7.7 Hz, 1H), 7.36 (s, 1H). HRMS (ESI) m/z: $[M+H]^+$ calcd for $C_{11}H_7Cl_2F_3N_3$, 307.9964; found, 307.9960.

1.2 Preparation of Intermediate III-1: 5-(4-methylpiperazin-1-yl)pyridin-2-amine 15 g (73.9 mmol) of 5-bromo-2-nitropyridine was weighed and added into a 250 mL round-bottomed flask, followed by dissolving with 100 mL of dimethyl sulfoxide, adding 15.3 g (110.7 mmol) of potassium carbonate, and stirring in an oil bath at 70° C. for 10 min. Subsequently, 12.7 g (126.1 mmol) of 1-methyl-piperazine was added and the reaction continued for 5 h. The reaction endpoint was detected by thin layer chromatography (petroleum ether: ethyl acetate=10:1). After the reaction was ended, the reaction was quenched with 300 mL of ice water. The resulting mixture was stirred for 30 min and extracted with ethyl acetate (three times, 200 mL each time). The extracted ethyl acetate layers were combined and washed three times with saturated sodium chloride solution. The washed ethyl acetate layer was dried with anhydrous sodium sulfate for 24 h, filtered, and concentrated. The obtained yellow residual solid was recrystallized with ethanol to obtain pure 1-methyl-4-(6-nitropyridine-3-yl)piperazine which is intermediate II-1. 2 g (9.0 mmol) of the 1-methyl-4-(6-nitropyridin-3-yl)piperazine was completely dissolved in methanol and subjected to catalytic hydrogenation in a high pressure reactor or a hydrogen-filled round-bottomed flask under the catalysis of 10% Pd/C (0.2 g). The reaction ended when the pressure in the high pressure reactor no longer decreased or the solution become clear. The reaction liquid was filtered to remove the catalyst and concentrated to obtain pure intermediate III-1. The intermediate III-1 was stored in a closed inert gas environment or used immediately.

1.3 Synthesis of Compound 41

A 25 mL sealed tube was taken for gas replacement with argon. 0.26 g (0.83 mmol) of the intermediate I-1, 0.2 g (1.00 mmol) of the intermediate III-1, 38 mg (0.042 mmol) of $Pd_2(dba)_3$, 83 mg (0.083 mmol) of 2,2'-bis(diphenylphosphino)-1,1'-binaphthyl (BINAP), and 1.2 g (1.25 mmol) of NaOtBu were added to the sealed tube, followed by stirring and dissolving with 10 mL of ultra-dry 1,4-dioxane. The sealed tube was sealed and the reaction was conducted at 110° C. for 12 h. After the reaction was ended, the sealed tube was cooled to room temperature. The reaction liquid was filtered, subjected to a reduced pressure treatment to remove solvent, and extracted with a water/ethyl acetate system. The ethyl acetate layer was dried with anhydrous sodium sulfate for 24 h, filtered, and concentrated to obtain a residue. The residue was purified and separated by an automated medium pressure chromatography system to obtain a white powder with a yield of 44% (0.17 g). mp 190-191° C.; $^1H$ NMR (600 MHz, Chloroform-d) δ 8.76 (s, 1H), 8.21 (s, 1H), 8.07 (d, J=2.9 Hz, 1H), 7.99 (d, J=9.0 Hz, 1H), 7.93 (s, 1H), 7.74 (d, J=8.0 Hz, 1H), 7.48 (t, J=7.9 Hz, 1H), 7.41 (d, J=7.7 Hz, 1H), 7.20 (dd, J=9.1, 2.9 Hz, 1H), 7.18 (s, 1H), 3.18-3.15 (m, 4H), 2.63-2.59 (m, 4H), 2.37 (s, 3H); $^{13}C$ NMR (151 MHz), Chloroform-d) δ 156.94, 155.35, 154.82, 145.84, 142.88, 138.38, 136.64, 131.30 (q, J=32.4 Hz), 129.44, 126.35, 124.71, 123.85 (q, J=272.5), 122.95, 120.83 (d, J=3.7 Hz), 118.22 (d, J=3.6 Hz), 113.12, 105.16, 54.90 (2C), 49.57 (2C), 46.12. HRMS (ESI) m/z: $[M+H]^+$ calcd for $C_{21}H_{22}ClF_3N_7$, 464.1572; found, 464.1572.

Embodiment 2

Synthesis of Compound 1: 5-chloro-$N^2$-phenyl-$N^4$-(3-(trifluoromethoxy)phenyl)pyrimidine-2,4-diamine (1)

Experimental steps are the same as those of Embodiment 1, except that the intermediate I-1 is replaced by an intermediate I-2 and the intermediate III-1 is replaced by aniline. White solid (yield: 77%). mp 142-144° C.; $^1H$ NMR (400 MHz, Chloroform-d) δ 8.13 (s, 1H), 7.70 (s, 1H), 7.53 (d, J=7.3 Hz, 2H), 7.47 (dd, J=8.2, 1.2 Hz, 1H), 7.43-7.32 (m, 3H), 7.16 (d, J=8.1 Hz, 2H), 7.10 (t, J=7.4 Hz, 1H), 7.05-6.98 (m, 1H). HRMS (ESI) m/z: $[M+H]^+$ calcd for $C_{17}H_{13}ClF_3N_{40}$, 381.0724; found, 381.0725.

Embodiment 3

Synthesis of Compound 2: 5-chloro-$N^2$,$N^4$-diphenylpyrimidine-2,4-diamine (2)

Experimental steps are the same as those of Embodiment 1, except that the intermediate I-1 is replaced by an intermediate I-3 and the intermediate III-1 is replaced by aniline. White solid (yield: 59%). mp 183-185° C.; $^1H$ NMR (400 MHz, Chloroform-d) δ 8.10 (s, 1H), 7.63 (d, J=7.5 Hz, 2H), 7.55 (d, J=7.6 Hz, 2H), 7.40 (t, J=7.9 Hz, 2H), 7.31 (t, J=7.9 Hz, 2H), 7.20 (t, J=7.5 Hz, 1H), 7.15 (s, 1H), 7.10 (s, 1H), 7.06 (t, J=7.4 Hz, 1H). HRMS (ESI) m/z: $[M+H]^+$ calcd for $C_{16}H_{14}ClN_4$, 297.0902; found, 297.0902.

Embodiment 4

Synthesis of Compound 3: 5-chloro-$N^2$-phenyl-$N^4$-(m-tolyl)pyrimidine-2,4-diamine (3)

Experimental steps are the same as those of Embodiment 1, except that the intermediate I-1 is replaced by an intermediate I-4 and the intermediate III-1 is replaced by aniline. White solid (yield: 68%). mp 181-183° C.; $^1H$ NMR (400 MHz, Chloroform-d) δ 8.09 (s, 1H), 7.56 (d, J=7.3 Hz, 2H), 7.46 (t, J=1.9 Hz, 1H), 7.42 (d, J=7.9 Hz, 1H), 7.31 (m, 3H), 7.20 (s, 1H), 7.10-7.01 (m, 2H), 7.01 (d, J=7.6 Hz, 1H), 2.39 (s, 3H). HRMS (ESI) m/z: $[M+H]^+$ calcd for $C_{17}H_{16}ClN_4$, 311.1058; found, 311.1058.

Embodiment 5

Synthesis of Compound 4: 5-chloro-$N^4$-(3-methoxyphenyl)-$N^2$-phenylpyrimidine-2,4-diamine (4)

Experimental steps are the same as those of Embodiment 1, except that the intermediate I-1 is replaced by an intermediate I-5 and the intermediate III-1 is replaced by aniline. White solid (yield: 50%). mp 145-146° C.; $^1H$ NMR (400 MHz, Chloroform-d) δ 8.10 (s, 1H), 7.56 (d, J=7.4 Hz, 2H), 7.35-7.25 (m, 4H), 7.23-7.12 (m, 2H), 7.11-7.01 (m, 2H), 6.74 (dd, J=8.2, 2.6 Hz, 1H), 3.79 (s, 3H). HRMS (ESI) m/z: $[M+H]^+$ calcd for $C_{17}H_{16}ClN_4O$, 327.1007; found, 327.1007.

Embodiment 6

Synthesis of Compound 5: 5-chloro-$N^4$-(3-ethylphenyl)-$N^2$-phenylpyrimidine-2,4-diamine (5)

Experimental steps are the same as those of Embodiment 1, except that the intermediate I-1 is replaced by an intermediate I-6 and the intermediate III-1 is replaced by aniline. White solid (yield: 64%). mp 147-150° C.; $^1H$ NMR (400 MHz, DMSO-$d_6$) δ 9.26 (s, 1H), 8.73 (s, 1H), 8.08 (s, 1H), 7.54 (d, J=7.5 Hz, 2H), 7.43 (d, J=8.0 Hz, 1H), 7.39 (t, J=1.9 Hz, 1H), 7.22 (t, J=7.8 Hz, 1H), 7.13-7.05 (m, 2H), 6.95 (d, J=7.9 Hz, 1H), 6.83 (t, J=7.3 Hz, 1H), 2.55 (q, J=7.6 Hz, 2H), 1.11 (t, J=7.6 Hz, 3H). HRMS (ESI) m/z: $[M+H]^+$ calcd for $C_{18}H_{18}ClN_4$, 325.1215; found, 325.1215.

Embodiment 7

Synthesis of Compound 6: 5-chloro-$N^4$-(3-isopropylphenyl)-$N^2$-phenylpyrimidine-2,4-diamine (6)

Experimental steps are the same as those of Embodiment 1, except that the intermediate I-1 is replaced by an intermediate I-7 and the intermediate III-1 is replaced by aniline. White solid (yield: 70%). mp 150-153° C.; $^1H$ NMR (400 MHz, DMSO-$d_6$) δ 9.24 (s, 1H), 8.72 (s, 1H), 8.07 (s, 1H), 7.52 (d, J=7.6 Hz, 2H), 7.49 (d, J=9.2 Hz, 1H), 7.34 (t, J=2.0 Hz, 1H), 7.22 (t, J=7.8 Hz, 1H), 7.12-7.04 (m, 2H), 6.98 (d, J=7.8 Hz, 1H), 6.82 (t, J=7.3 Hz, 1H), 2.81 (p, J=6.9 Hz, 1H), 1.14 (d, J=6.9 Hz, 6H). HRMS (ESI) m/z: $[M+H]^+$ calcd for $C_{19}H_{20}ClN_4$, 339.1371; found, 339.1371.

Embodiment 8

Synthesis of Compound 7: N-(3-((5-chloro-2-(phenylamino)pyrimidin-4-yl)amino)phenyl)acetamide (7)

Experimental steps are the same as those of Embodiment 1, except that the intermediate I-1 is replaced by an intermediate I-8 and the intermediate III-1 is replaced by aniline. White solid (yield: 67%). mp 208-210° C.; $^1H$ NMR (400 MHz, DMSO-$d_6$) δ 9.96 (s, 1H), 9.31 (s, 1H), 8.93 (s, 1H), 8.14 (s, 1H), 7.79 (s, 1H), 7.60 (d, J=8.0 Hz, 2H), 7.38 (d, J=3.9 Hz, 1H), 7.27 (d, J=5.6 Hz, 2H), 7.11 (t, J=7.8 Hz, 2H), 6.86 (t, J=7.3 Hz, 1H), 2.03 (s, 3H). HRMS (ESI) m/z: $[M+H]^+$ calcd for $C_{18}H_{17}ClN_5O$, 354.1116; found, 354.1117.

Embodiment 9

Synthesis of compound 8: 5-chloro-$N^4$-(3-fluorophenyl)-$N^2$-phenylpyrimidine-2,4-diamine (8) Experimental steps are the same as those of Embodiment 1, except that the intermediate I-1 is replaced by an intermediate I-9 and the intermediate III-1 is replaced by aniline. White solid (yield: 40%). mp 181-183° C.; $^1H$ NMR (400 MHz, DMSO-$d_6$) δ 9.42 (s, 1H), 8.97 (s, 1H), 8.19 (s, 1H), 7.70 (d, J=11.8 Hz, 1H), 7.62 (d, J=7.4 Hz, 2H), 7.53 (d, J=8.1 Hz, 1H), 7.36 (td, J=8.2, 6.8 Hz, 1H), 7.29-7.16 (m, 2H), 7.02-6.88 (m, 2H). HRMS (ESI) m/z: $[M+H]^+$ calcd for $C_{16}H_{13}ClFN_4$, 315.0807; found, 315.0806.

Embodiment 10

Synthesis of Compound 9: 5-chloro-$N^2$-phenyl-$N^4$-(3-(trifluoromethyl)phenyl)pyrimidine-2,4-diamine (9)

Experimental steps are the same as those of Embodiment 1, except that the intermediate III-1 is replaced by aniline. White solid (yield: 68%). mp 160.5-161.2° C.; $^1H$ NMR (400 MHz, Chloroform-d) δ 8.11 (s, 1H), 7.86 (s, 1H), 7.82 (d, J=8.2 Hz, 1H), 7.53-7.45 (m, 3H), 7.40 (d, J=7.8 Hz, 1H), 7.30 (t, J=7.9 Hz, 2H), 7.15 (d, J=3.6 Hz, 2H), 7.05 (t, J=7.4 Hz, 1H). HRMS (ESI) m/z: $[M+H]^+$ calcd for $C_{16}H_{13}ClFN_4$, 365.0775; found, 365.0775.

Embodiment 11

Synthesis of Compound 10: 5-chloro-$N^4$-(4-fluorophenyl)-$N^2$-phenylpyrimidine-2,4-diamine (10)

Experimental steps are the same as those of Embodiment 1, except that the intermediate I-1 is replaced by an intermediate I-10 and the intermediate III-1 is replaced by aniline. White solid (yield: 66%). mp 195-197° C.; $^1H$ NMR (400 MHz, Chloroform-d) δ 8.09 (s, 1H), 7.56 (m, 2H), 7.51 (d, J=8.0 Hz, 2H), 7.32 (s, 1H), 7.29 (d, J=6.0 Hz, 2H), 7.16-6.99 (m, 4H). HRMS (ESI) m/z: $[M+H]^+$ calcd for $C_{16}H_{13}ClFN_4$, 315.0807; found, 315.0807.

Embodiment 12

Synthesis of Compound 11: 5-chloro-$N^2$-phenyl-$N^4$-(4-(trifluoromethyl)phenyl)pyrimidine-2,4-diamine (11)

Experimental steps are the same as those of Embodiment 1, except that the intermediate I-1 is replaced by an intermediate I-11 and the intermediate III-1 is replaced by aniline. White solid (yield: 30%). mp 193-196° C.; $^1H$ NMR (400 MHz, DMSO-$d_6$) δ 9.44 (s, 1H), 9.18 (s, 1H), 8.23 (s, 1H), 7.96 (d, J=8.4 Hz, 2H), 7.68 (d, J=8.5 Hz, 2H), 7.61 (d, J=8.0 Hz, 2H), 7.21 (t, J=7.9 Hz, 2H), 6.94 (t, J=7.3 Hz, 1H). HRMS (ESI) m/z: $[M+H]^+$ calcd for $C_{17}H_{13}ClF_3N_4$, 365.0775; found, 365.0776.

Embodiment 13

Synthesis of Compound 12: 5-chloro-$N^2$-phenyl-$N^4$-(4-(trifluoromethoxy)phenyl)pyrimidine-2,4-diamine (12)

Experimental steps are the same as those of Embodiment 1, except that the intermediate I-1 is replaced by an intermediate I-12 and the intermediate III-1 is replaced by aniline. White solid (yield: 60%). mp 188-190° C.; $^1H$ NMR (400 MHz, DMSO-$d_6$) δ 9.38 (s, 1H), 9.05 (s, 1H), 8.18 (s, 1H), 7.78 (d, J=9.0 Hz, 2H), 7.59 (d, J=8.1 Hz, 2H), 7.35 (d, J=8.1 Hz, 2H), 7.22-7.07 (m, 2H), 6.91 (t, J=7.3 Hz, 1H). HRMS (ESI) m/z: $[M+H]^+$ calcd for $C_{17}H_{13}ClF_3N_{40}$, 381.0724; found, 381.0726.

Embodiment 14

Synthesis of Compound 13: 5-chloro-$N^4$-(4-fluoro-3-(trifluoromethyl)phenyl)-$N^2$-phenylpyrimidine-2,4-diamine (13)

Experimental steps are the same as those of Embodiment 1, except that the intermediate I-1 is replaced by an intermediate I-13 and the intermediate III-1 is replaced by aniline. White solid (yield: 63%). mp 160-163° C.; $^1H$ NMR (400 MHz, Chloroform-d) δ 8.14 (s, 1H), 7.81 (dd, J=7.3, 4.6 Hz, 2H), 7.48 (d, J=7.2 Hz, 2H), 7.35-7.27 (m, 2H), 7.21 (t, J=9.5 Hz, 1H), 7.16 (s, 1H), 7.12-7.04 (m, 2H). HRMS (ESI) m/z: $[M+H]^+$ calcd for $C_{17}H_{12}ClF_4N_4$, 383.0681; found, 383.0683.

Embodiment 15

Synthesis of Compound 14: 5-chloro-$N^2$-cyclopropyl-$N^4$-(3-(trifluoromethyl)phenyl)pyrimidine-2,4-diamine (14)

Experimental steps are the same as those of Embodiment 1, except that the intermediate III-1 is replaced by cyclopropylamine. White solid (yield: 59%). mp 138.5-139.1° C.; $^{1}H$ NMR (400 MHz, Chloroform-d) δ 8.45 (s, 1H), 8.03 (s, 1H), 7.72 (d, J=8.2 Hz, 1H), 7.46 (t, J=7.9 Hz, 1H), 7.36 (d, J=7.8 Hz, 1H), 7.17 (s, 1H), 5.39 (s, 1H), 2.77 (m, 1H), 0.86 (m, 2H), 0.66-0.50 (m, 2H). HRMS (ESI) m/z: $[M+H]^+$ calcd for $C_{14}H_{13}ClF_3N_4$, 329.0775; found, 329.0777.

Embodiment 16

Synthesis of Compound 15: 5-chloro-$N^2$-cyclopentyl-$N^4$-(3-(trifluoromethyl)phenyl)pyrimidine-2,4-diamine (15)

Experimental steps are the same as those of Embodiment 1, except that the intermediate III-1 is replaced by cyclopentylamine. White solid (yield: 61%). mp 117.2-118.2° C.; $^{1}H$ NMR (400 MHz, Chloroform-d) δ 8.46 (s, 1H), 7.99 (s, 1H), 7.62 (s, 1H), 7.47 (t, J=7.9 Hz, 1H), 7.36 (d, J=8.4 Hz, 1H), 7.13 (s, 1H), 5.10 (s, 1H), 4.37-4.08 (m, 1H), 2.08 (m, 2H), 1.82-1.60 (m, 4H), 1.50 (m, 2H). HRMS (ESI) m/z: $[M+H]^+$ calcd for $C_{16}H_{17}ClF_3N_4$, 357.1088; found, 357.1089.

Embodiment 17

Synthesis of Compound 16: 5-chloro-$N^2$-cyclohexyl-$N^4$-(3-(trifluoromethyl)phenyl)pyrimidine-2,4-diamine (16)

Experimental steps are the same as those of Embodiment 1, except that the intermediate III-1 is replaced by cyclohexylamine. White solid (yield: 57%). mp 155.7-158.1° C.; $^{1}H$ NMR (400 MHz, DMSO-$d_6$) δ 8.85 (s, 1H), 8.28 (s, 1H), 7.98 (s, 2H), 7.50 (t, J=8.0 Hz, 1H), 7.34 (d, J=7.7 Hz, 1H), 7.01 (s, 1H), 3.54 (s, 1H), 1.81 (s, 2H), 1.66 (s, 2H), 1.55 (m, 1H), 1.33-1.01 (m, 5H). HRMS (ESI) m/z: $[M+H]^+$ calcd for $C_{17}H_{19}ClF_3N_4$, 371.1245; found, 371.1244.

Embodiment 18

Synthesis of Compound 17: $N^2$-benzyl-5-chloro-$N^4$-(3-(trifluoromethyl)phenyl)pyrimidine-2,4-diamine (17)

Experimental steps are the same as those of Embodiment 1, except that the intermediate III-1 is replaced by benzylamine. White solid (yield: 39%). mp 120.3-121.3° C.; $^{1}H$ NMR (400 MHz, DMSO-$d_6$) δ 8.90 (s, 1H), 8.13 (s, 1H), 8.04 (s, 1H), 7.88-7.07 (m, 9H), 4.42 (d, J=4.5 Hz, 2H). HRMS (ESI) m/z: $[M+H]^+$ calcd for $C_{18}H_{15}ClF_3N_4$, 379.0932; found, 379.0933.

Embodiment 19

Synthesis of Compound 18: 5-chloro-$N^2$-phenethyl-$N^4$-(3-(trifluoromethyl)phenyl)pyrimidine-2,4-diamine (18)

Experimental steps are the same as those of Embodiment 1, except that the intermediate III-1 is replaced by phenethylamine. White solid (yield: 35%). mp 107-108.2° C.; $^{1}H$ NMR (400 MHz, DMSO-$d_6$) δ 8.93 (s, 1H), 8.24 (s, 1H), 8.02 (s, 2H), 7.51 (t, J=8.0 Hz, 1H), 7.38 (d, J=7.6 Hz, 1H), 7.28-7.05 (m, 6H), 3.41 (d, J=4.7 Hz, 2H), 2.77 (s, 2H). HRMS (ESI) m/z: [M+H]+ calcd for $C_{19}H_{17}ClF_3N_4$, 393.1088; found, 393.1088.

Embodiment 20

Synthesis of Compound 19: 5-chloro-$N^2$-(p-tolyl)-$N^4$-(3-(trifluoromethyl)phenyl)pyrimidine-2,4-diamine (19)

Experimental steps are the same as those of Embodiment 1, except that the intermediate III-1 is replaced by p-toluidine. White solid (yield: 53%). mp 160-161.2° C.; $^{1}H$ NMR (400 MHz, Chloroform-d) δ 8.11 (s, 1H), 7.87 (s, 1H), 7.84 (d, J=8.7 Hz, 1H), 7.49 (t, J=7.9 Hz, 1H), 7.42 (d, J=7.8 Hz, 1H), 7.38 (d, J=8.4 Hz, 2H), 7.13 (q, J=9.2, 8.2 Hz, 4H), 2.35 (s, 3H). HRMS (ESI) m/z: $[M+H]^+$ calcd for $C_{18}H_{15}ClF_3N_4$, 379.0932; found, 379.0932.

Embodiment 21

Synthesis of Compound 20: 5-chloro-$N^2$-(p-methoxyphenyl)-$N^4$-(3-(trifluoromethyl)phenyl)pyrimidine-2,4-diamine (20)

Experimental steps are the same as those of Embodiment 1, except that the intermediate III-1 is replaced by p-methoxyaniline. White solid (yield: 39%). mp 184.7-185.2° C.; $^{1}H$ NMR (400 MHz, Chloroform-d) δ 8.10 (s, 1H), 7.89 (s, 1H), 7.80 (d, J=8.1 Hz, 1H), 7.47 (t, J=7.9 Hz, 1H), 7.39 (d, J=8.8 Hz, 2H), 7.16 (s, 1H), 6.89 (m, 3H), 3.83 (s, 3H). HRMS (ESI) m/z: $[M+H]^+$ calcd for $C_{18}H_{15}ClF_3N_{40}$, 395.0881; found, 395.0880.

Embodiment 22

Synthesis of Compound 21: 5-chloro-$N^2$-(p-ethylphenyl)-$N^4$-(3-(trifluoromethyl)phenyl)pyrimidine-2,4-diamine (21)

Experimental steps are the same as those of Embodiment 1, except that the intermediate III-1 is replaced by p-ethylaniline. White solid (yield: 48%). mp 155-156.4° C.; $^{1}H$ NMR (400 MHz, Chloroform-d) δ 8.12 (s, 1H), 7.88 (s, 1H), 7.84 (d, J=8.2 Hz, 1H), 7.48 (t, J=7.9 Hz, 1H), 7.41 (m, 3H), 7.16 (d, J=8.4 Hz, 2H), 7.10 (s, 1H), 2.65 (q, J=7.6 Hz, 2H), 1.26 (t, J=7.6 Hz, 3H). HRMS (ESI) m/z: $[M+H]^+$ calcd for $C_{19}H_{17}ClF_3N_4$, 393.1088; found, 393.1087.

Embodiment 23

Synthesis of Compound 22: 5-chloro-$N^2$-(p-isopropylphenyl)-$N^4$-(3-(trifluoromethyl)phenyl)pyrimidine-2,4-diamine (22)

Experimental steps are the same as those of Embodiment 1, except that the intermediate III-1 is replaced by p-isopropylaniline. White solid (yield: 57%). mp 185.3-186.1° C.; $^{1}H$ NMR (400 MHz, Chloroform-d) δ 8.12 (s, 1H), 7.90 (s, 1H), 7.84 (d, J=8.0 Hz, 1H), 7.48 (t, J=7.9 Hz, 1H), 7.45-7.40 (m, 3H), 7.19 (d, J=8.5 Hz, 2H), 7.17 (s, 1H), 7.12 (s, 1H), 2.98-2.86 (m, 1H), 1.28 (d, J=6.9 Hz, 6H). HRMS (ESI) m/z: $[M+H]^+$ calcd for $C_{20}H_{19}ClF_3N_4$, 407.1245; found, 407.1246.

Embodiment 24

Synthesis of Compound 23: 5-chloro-$N^2$-(p-tert-butylphenyl)-$N^4$-(3-(trifluoromethyl)phenyl)pyrimidine-2,4-diamine (23)

Experimental steps are the same as those of Embodiment 1, except that the intermediate III-1 is replaced by p-tertbutylaniline. White solid (yield: 62%). mp 211-211.8° C.; $^1$H NMR (400 MHz, Chloroform-d) δ 8.12 (s, 1H), 7.92 (s, 1H), 7.83 (d, J=8.1 Hz, 1H), 7.48 (t, J=7.8 Hz, 2H), 7.43 (d, J=8.7 Hz, 2H), 7.35 (d, J=8.7 Hz, 1H), 7.29 (s, 1H), 7.17 (s, 1H), 7.05 (s, 1H), 1.35 (s, 9H). HRMS (ESI) m/z: $[M+H]^+$ calcd for $C_{21}H_{21}ClF_3N_4$, 421.1401; found, 421.1402.

Embodiment 25

Synthesis of Compound 24: 5-chloro-$N^2$-(p-fluorophenyl)-$N^4$-(3-(trifluoromethyl)phenyl)pyrimidine-2,4-diamine (24)

Experimental steps are the same as those of Embodiment 1, except that the intermediate III-1 is replaced by p-fluoroaniline. White solid (yield: 63%). mp 157.6-158° C.; $^1$H NMR (400 MHz, Chloroform-d) δ 8.12 (s, 1H), 7.89 (s, 1H), 7.78 (d, J=9.3 Hz, 1H), 7.49 (t, J=7.9 Hz, 1H), 7.46 (d, J=4.8 Hz, 1H), 7.43 (m, 2H), 7.18 (s, 1H), 7.06 (s, 1H), 7.01 (t, J=8.7 Hz, 2H). IRMS (ESI) m/z: $[M+H]^+$ calcd for $C_{17}H_{12}ClF_4N_4$, 383.0681; found, 383.0681.

Embodiment 26

Synthesis of Compound 25: 5-chloro-$N^2$-(p-trifluoromethoxyphenyl)-$N^4$-(3-(trifluoromethyl)phenyl)pyrimidine-2,4-diamine (25)

Experimental steps are the same as those of Embodiment 1, except that the intermediate III-1 is replaced by p-trifluoromethoxyaniline. White solid (yield: 59%). mp 129.2-130.1° C.; $^1$H NMR (400 MHz, Chloroform-d) δ 8.14 (s, 1H), 7.90 (s, 1H), 7.77 (d, J=8.1 Hz, 1H), 7.52 (m, 3H), 7.46 (t, J=8.3 Hz, 1H), 7.25-7.11 (m, 4H). HRMS (ESI) m/z: $[M+H]^+$ calcd for $C_{18}H_{12}ClF_6N_{40}$, 449.0598; found, 449.0600.

Embodiment 27

Synthesis of Compound 26: 5-chloro-$N^2$-(p-carboxamidophenyl)-$N^4$-(3-(trifluoromethyl)phenyl)pyrimidine-2,4-diamine (26)

Experimental steps are the same as those of Embodiment 1, except that the intermediate III-1 is replaced by p-carboxamidoaniline. White solid (yield: 89%). mp 250.0-250.8° C.; $^1$H NMR (400 MHz, DMSO-$d_6$) δ 9.71 (s, 1H), 9.24 (s, 1H), 8.27 (s, 1H), 8.12 (d, J=8.1 Hz, 1H), 7.94 (t, J=2.0 Hz, 1H), 7.78 (s, 1H), 7.71 (d, J=8.8 Hz, 2H), 7.68-7.61 (m, 3H), 7.51 (d, J=7.8 Hz, 1H), 7.16 (s, 1H). HRMS (ESI) m/z: $[M+H]^+$ calcd for $C_{18}H_{14}ClF_3N_5O$, 408.0833; found, 408.0833.

Embodiment 28

Synthesis of Compound 27: 5-chloro-$N^2$-(p-carbamoylphenyl)-$N^4$-(3-(trifluoromethyl)phenyl)pyrimidine-2,4-diamine (27)

Experimental steps are the same as those of Embodiment 1, except that the intermediate III-1 is replaced by p-carbamoylaniline. White solid (yield: 40%). mp 225.0-226.0° C.; $^1$H NMR (400 MHz, DMSO-$d_6$) δ 9.79 (s, 1H), 9.34 (s, 1H), 9.11 (s, 1H), 8.18 (s, 1H), 8.11 (d, J=8.2 Hz, 1H), 7.95 (t, J=2.0 Hz, 1H), 7.56 (t, J=8.0 Hz, 1H), 7.50-7.44 (m, 3H), 7.38 (d, J=9.0 Hz, 2H), 2.01 (s, 3H). HRMS (ESI) m/z: $[M+H]^+$ calcd for $C_{19}H_{16}ClF_3N_5O$, 422.0990; found, 422.0991.

Embodiment 29

Synthesis of Compound 28: 5-chloro-$N^2$-(p-methanesulfonylphenyl)-$N^4$-(3-(trifluoromethyl)phenyl)pyrimidine-2,4-diamine (28)

Experimental steps are the same as those of Embodiment 1, except that the intermediate III-1 is replaced by p-methanesulfonylaniline. White solid (yield: 15%). mp 240-241° C.; $^1$H NMR (400 MHz, DMSO-$d_6$) δ 9.99 (s, 1H), 9.31 (s, 1H), 8.30 (s, 1H), 8.07 (d, J=7.8 Hz, 1H), 7.95 (s, 1H), 7.83 (d, J=8.9 Hz, 2H), 7.66 (m, 3H), 7.54 (d, J=8.9 Hz, 1H), 3.12 (s, 3H). HRMS (ESI) m/z: $[M+H]^+$ calcd for $C_{18}H_{15}ClF_3N_4O_2S$, 443.0551; found, 443.0551.

Embodiment 30

Synthesis of Compound 29: 5-chloro-$N^2$-(p-cyanophenyl)-$N^4$-(3-(trifluoromethyl)phenyl)pyrimidine-2,4-diamine (29)

Experimental steps are the same as those of Embodiment 1, except that the intermediate III-1 is replaced by p-cyanoaniline. White solid (yield: 12%). mp 216.9-217.3° C.; $^1$H NMR (400 MHz, DMSO-$d_6$) δ 9.98 (s, 1H), 9.31 (s, 1H), 8.30 (s, 1H), 8.06 (d, J=7.3 Hz, 1H), 7.93 (s, 1H), 7.77 (d, J=8.8 Hz, 2H), 7.66 (t, J=8.0 Hz, 1H), 7.57 (d, J=8.8 Hz, 2H), 7.52 (d, J=7.2 Hz, 1H). HRMS (ESI) m/z: $[M+H]^+$ calcd for $C_{18}H_{12}ClF_3N_5$, 390.0728; found, 390.0725.

Embodiment 31

Synthesis of Compound 30: 5-chloro-$N^2$-(pyridin-2-ylmethyl)-$N^4$-(3-(trifluoromethyl)phenyl)pyrimidine-2,4-diamine (30)

Experimental steps are the same as those of Embodiment 1, except that the intermediate III-1 is replaced by 2-aminomethylpyridine. White solid (yield: 34%). mp 135.1-136.1° C.; $^1$H NMR (400 MHz, Chloroform-d) δ 8.60 (d, J=5.0 Hz, 1H), 8.27 (s, 1H), 8.05 (s, 1H), 7.66 (t, J=8.5 Hz, 1H), 7.44 (t, J=7.9 Hz, 1H), 7.36 (d, J=7.8 Hz, 1H), 7.33-7.24 (m, 2H), 7.21 (t, J=6.3 Hz, 1H), 7.14 (s, 1H), 6.24 (s, 1H), 4.73 (s, 2H). HRMS (ESI) m/z: $[M+H]^+$ calcd for $C_{17}H_{14}ClF_3N_5$, 380.0884; found, 380.0884.

Embodiment 32

Synthesis of Compound 31: 5-chloro-$N^2$-(pyridin-3-ylmethyl)-$N^4$-(3-(trifluoromethyl)phenyl)pyrimidine-2,4-diamine (31)

Experimental steps are the same as those of Embodiment 1, except that the intermediate III-1 is replaced by 3-aminomethylpyridine. White solid (yield: 45%). mp 171.9-172.2° C.; $^1$H NMR (400 MHz, Chloroform-d) δ 8.60 (s, 1H), 8.53 (d, J=4.8 Hz, 1H), 8.07 (s, 1H), 7.99 (s, 1H), 7.66 (m, 2H), 7.48-7.22 (m, 4H), 7.16 (s, 1H), 4.63 (d, J=6.1 Hz, 2H). HRMS (ESI) m/z: $[M+H]^+$ calcd for $C_{17}H_{14}ClF_3N_5$, 380.0884; found, 380.0884.

Embodiment 33

Synthesis of Compound 32: 5-chloro-$N^2$-(pyridin-4-ylmethyl)-$N^4$-(3-(trifluoromethyl)phenyl)pyrimidine-2,4-diamine (32)

Experimental steps are the same as those of Embodiment 1, except that the intermediate III-1 is replaced by 4-aminomethylpyridine. White solid (yield: 42%). mp 163.1-164.2° C.; $^1$H NMR (400 MHz, Chloroform-d) δ 8.56 (d, J=4.1 Hz, 2H), 8.03 (s, 2H), 7.37 (d, J=8.7 Hz, 2H), 7.29 (s, 1H), 7.25 (d, J=5.0 Hz, 2H), 7.14 (s, 1H), 5.63 (s, 1H), 4.64 (d, J=6.3 Hz, 2H). HRMS (ESI) m/z: $[M+H]^+$ calcd for $C_{17}H_{14}ClF_3N_5$, 380.0884; found, 380.0885.

Embodiment 34

Synthesis of Compound 33: 5-chloro-$N^2$-(2-(pyridin-2-yl)ethyl)-$N^4$-(3-(trifluoromethyl)phenyl)pyrimidine-2,4-diamine (33)

Experimental steps are the same as those of Embodiment 1, except that the intermediate III-1 is replaced by 2-aminoethylpyridine. White solid (yield: 43%). mp 120-121.1° C.; $^1$H NMR (400 MHz, Chloroform-d) δ 8.57 (d, J=3.8 Hz, 1H), 8.32 (s, 1H), 7.99 (s, 1H), 7.68 (d, J=8.1 Hz, 1H), 7.61 (t, J=7.7 Hz, 1H), 7.47 (t, J=8.0 Hz, 1H), 7.36 (d, J=7.8 Hz, 1H), 7.20-7.10 (m, 3H), 5.72 (s, 1H), 3.84 (q, J=6.2 Hz, 2H), 3.11 (t, J=6.5 Hz, 2H). HRMS (ESI) m/z: $[M+H]^+$ calcd for $C_{18}H_{16}ClF_3N_5$, 394.1041; found, 394.1042.

Embodiment 35

Synthesis of Compound 34: 5-chloro-$N^2$-(2-(pyridin-3-yl)ethyl)-$N^4$-(3-(trifluoromethyl)phenyl)pyrimidine-2,4-diamine (34)

Experimental steps are the same as those of Embodiment 1, except that the intermediate III-1 is replaced by 3-aminoethylpyridine. White solid (yield: 53%). mp 158-159° C.; $^1$H NMR (400 MHz, Chloroform-d) δ 8.49 (d, J=5.2 Hz, 2H), 7.99 (s, 1H), 7.67 (t, J=6.7 Hz, 1H), 7.57-7.45 (m, 1H), 7.39 (d, J=7.8 Hz, 2H), 7.30-7.19 (m, 2H), 7.16 (s, 1H), 5.25 (s, 1H), 3.68 (q, J=6.6 Hz, 2H), 2.93 (t, J=6.8 Hz, 2H). HRMS (ESI) m/z: $[M+H]^+$ calcd for $C_{18}H_{16}ClF_3N_5$, 394.1041; found, 394.1041.

Embodiment 36

Synthesis of Compound 35: 5-chloro-$N^2$-(pyridin-2-yl)-$N^4$-(3-(trifluoromethyl)phenyl)pyrimidine-2,4-diamine (35)

Experimental steps are the same as those of Embodiment 1, except that the intermediate III-1 is replaced by 2-aminopyridine. White solid (yield: 57%). mp 135.7-136.3° C.; $^1$H NMR (400 MHz, Chloroform-d) δ 8.31 (dd, J=4.9, 1.0 Hz, 1H), 8.22 (s, 2H), 8.13 (d, J=8.5 Hz, 1H), 7.92 (s, 1H), 7.77 (d, J=8.0 Hz, 1H), 7.62-7.55 (m, 1H), 7.51 (t, J=7.9 Hz, 1H), 7.44 (d, J=7.8 Hz, 1H), 7.19 (s, 1H), 6.92 (ddd, J=7.2, 5.0, 0.8 Hz, 1H). HRMS (ESI) m/z: $[M+H]^+$ calcd for $C_{16}H_{12}ClF_3N_5$, 366.0728; found, 366.0726.

Embodiment 37

Synthesis of Compound 36: 5-chloro-$N^2$-(pyridin-3-yl)-$N^4$-(3-(trifluoromethyl)phenyl)pyrimidine-2,4-diamine (36)

Experimental steps are the same as those of Embodiment 1, except that the intermediate III-1 is replaced by 3-aminopyridine. White solid (yield: 23%). mp 218.1-219.3° C.; $^1$H NMR (400 MHz, DMSO-$d_6$) δ 9.61 (s, 1H), 9.22 (s, 1H), 8.69 (d, J=2.5 Hz, 1H), 8.25 (s, 1H), 8.11 (dd, J=4.6, 1.4 Hz, 1H), 8.07 (d, J=8.2 Hz, 1H), 8.02 (d, J=8.4 Hz, 1H), 7.93 (s, 1H), 7.59 (t, J=7.9 Hz, 1H), 7.48 (d, J=7.7 Hz, 1H), 7.15 (dd, J=8.3, 4.7 Hz, 1H). HRMS (ESI) m/z: $[M+H]^+$ calcd for $C_{16}H_{12}ClF_3N_5$, 366.0728; found, 366.0728.

Embodiment 38

Synthesis of Compound 37: 5-chloro-$N^2$-(pyridin-4-yl)-$N^4$-(3-(trifluoromethyl)phenyl)pyrimidine-2,4-diamine (37)

Experimental steps are the same as those of Embodiment 1, except that the intermediate III-1 is replaced by 4-aminopyridine. White solid (yield: 35%). mp 223-224° C.; $^1$H NMR (400 MHz, DMSO-$d_6$) δ 9.89 (s, 1H), 9.33 (s, 1H), 8.31 (s, 1H), 8.20 (d, J=6.3 Hz, 1H), 8.04 (d, J=8.2 Hz, 2H), 7.94 (s, 1H), 7.65 (t, J=7.9 Hz, 1H), 7.54 (m, 3H). HRMS (ESI) m/z: $[M+H]^+$ calcd for $C_{16}H_{12}ClF_3N_5$, 366.0728; found, 366.0728.

Embodiment 39

Synthesis of Compound 38: 5-chloro-$N^2$-(pyrimidin-5-yl)-$N^4$-(3-(trifluoromethyl)phenyl)pyrimidine-2,4-diamine (38)

Experimental steps are the same as those of Embodiment 1, except that the intermediate III-1 is replaced by 4-aminopyrimidine. White solid (yield: 77%). mp 213-214° C.; $^1$H NMR (400 MHz, DMSO-$d_6$) δ 10.47 (s, 1H), 9.28 (s, 1H), 8.81 (d, J=4.6 Hz, 1H), 8.30 (s, 1H), 8.26 (d, J=7.9 Hz, 1H), 8.18 (d, J=9.1 Hz, 1H), 7.99 (s, 1H), 7.59 (t, J=8.0 Hz, 1H), 7.53-7.35 (m, 2H). HRMS (ESI) m/z: $[M+H]^+$ calcd for $C_{15}H_{11}ClF_3N_6$, 367.0680; found, 367.0681.

Embodiment 40

Synthesis of Compound 39: 5-chloro-$N^2$-(pyridazin-3-yl)-$N^4$-(3-(trifluoromethyl)phenyl)pyrimidine-2,4-diamine (39)

Experimental steps are the same as those of Embodiment 1, except that the intermediate III-1 is replaced by 3-aminopyridazine. White solid (yield: 67%). mp 188-189° C.; $^1$H NMR (400 MHz, DMSO-$d_6$) δ 9.75 (s, 1H), 9.31 (s, 1H), 8.97 (s, 2H), 8.71 (s, 1H), 8.28 (s, 1H), 8.05 (d, J=8.0 Hz, 1H), 7.90 (s, 1H), 7.59 (t, J=8.0 Hz, 1H), 7.49 (d, J=7.7 Hz, 1H). HRMS (ESI) m/z: $[M+H]^+$ calcd for $C_{15}H_{11}ClF_3N_6$, 367.0680; found, 367.0677.

Embodiment 41

Synthesis of Compound 40: 5-chloro-$N^2$-(4-(4-methylpiperazin-1-yl)phenyl)-$N^4$-(3-(trifluoromethyl)phenyl)pyrimidine-2,4-diamine (40)

Experimental steps are the same as those of Embodiment 1, except that the intermediate III-1 is replaced by an intermediate III-2. White solid (yield: 71%). mp 140-144° C.; $^1$H NMR (600 MHz, Chloroform-d) δ 8.04 (s, 1H), 7.86 (s, 1H), 7.79 (d, J=8.1 Hz, 1H), 7.43 (t, J=7.9 Hz, 1H), 7.38 (s, 1H), 7.36 (d, J=8.9 Hz, 2H), 7.14 (s, 1H), 6.88 (d, J=8.9 Hz, 2H), 3.23-3.15 (m, 4H), 2.75-2.62 (m, 4H), 2.40 (s, 3H). HRMS (ESI) m/z: $[M+H]^+$ calcd for $C_{22}H_{23}ClF_3N_6$, 463.1619; found, 463.1619.

Embodiment 42

Synthesis of Compound 42: 5-chloro-$N^2$-(6-(4-methylpiperazin-1-yl)pyridin-3-yl)-$N^4$-(3-(trifluoromethyl)phenyl)pyrimidine-2,4-diamine (42)

Experimental steps are the same as those of Embodiment 1, except that the intermediate III-1 is replaced by an intermediate III-3. White solid (yield: 47%). mp 169-171° C.; $^1$H NMR (600 MHz, Chloroform-d) δ 8.16 (d, J=2.5 Hz, 1H), 8.05 (s, 1H), 7.85 (s, 1H), 7.72 (dd, J=9.0, 2.7 Hz, 2H), 7.42 (t, J=8.0 Hz, 1H), 7.35 (d, J=8.1 Hz, 1H), 7.13 (s, 1H), 6.88 (s, 1H), 6.63 (d, J=9.0 Hz, 1H), 3.56-3.51 (m, 4H), 2.57-2.52 (m, 4H), 2.36 (s, 3H). HRMS (ESI) m/z: $[M+H]^+$ calcd for $C_{21}H_{22}ClF_3N_7$, 464.1572; found, 464.1573.

Embodiment 43

Synthesis of Compound 43: 5-chloro-$N^2$-(2-(4-methylpiperazin-1-yl)pyrimidin-5-yl)-$N^4$-(3-(trifluoromethyl)phenyl)pyrimidine-2,4-diamine (43)

Experimental steps are the same as those of Embodiment 1, except that the intermediate III-1 is replaced by an intermediate III-4. White solid (yield: 32%). mp 195-197° C.; $^1$H NMR (600 MHz, Chloroform-d) δ 8.24 (d, J=2.8 Hz, 1H), 8.16 (s, 1H), 8.13 (d, J=9.8 Hz, 1H), 7.91 (s, 1H), 7.69 (d, J=7.9 Hz, 1H), 7.50 (t, J=7.9 Hz, 1H), 7.43 (d, J=7.8 Hz, 1H), 7.20 (s, 1H), 6.89 (d, J=9.8 Hz, 1H), 3.61-3.56 (m, 4H), 2.58-2.54 (m, 4H), 2.36 (s, 3H). HRMS (ESI) m/z: $[M+H]^+$ calcd for $C_{20}H_{21}ClF_3N_8$, 465.1524; found, 465.1525.

Embodiment 44

Synthesis of Compound 44: 5-chloro-$N^2$-(6-(4-methylpiperazin-1-yl)pyridazin-3-yl)-$N^4$-(3-(trifluoromethyl)phenyl)pyrimidine-2,4-di Amine (44)

Experimental steps are the same as those of Embodiment 1, except that the intermediate III-1 is replaced by an intermediate III-5. White solid (yield: 54%). mp 190-193° C.; $^1$H NMR (600 MHz, Chloroform-d) δ 8.27 (s, 1H), 8.23 (s, 1H), 7.83 (s, 1H), 7.47 (d, J=7.2 Hz, 2H), 7.29-7.23 (m, 3H), 7.22 (s, 1H), 3.91 (s, 4H), 2.52 (t, J=4.8 Hz, 4H), 2.37 (s, 3H). HRMS (ESI) m/z: $[M+H]^+$ calcd for $C_{20}H_{21}ClF_3N_8$, 465.1524; found, 465.1525.

Embodiment 45

Synthesis of Compound 45: 5-chloro-$N^2$-(5-(4-ethylpiperazin-1-yl)pyridin-2-yl)-$N^4$-(3-(trifluoromethyl)phenyl)pyrimidine-2,4-diamine (45)

Experimental steps are the same as those of Embodiment 1, except that the intermediate III-1 is replaced by an intermediate III-6. White solid (yield: 54%). mp 184-186° C.; $^1$H NMR (400 MHz, Chloroform-d) δ 8.36 (s, 1H), 8.20 (s, 1H), 8.05 (d, J=2.9 Hz, 1H), 8.01 (d, J=9.1 Hz, 1H), 7.95 (s, 1H), 7.78 (d, J=7.4 Hz, 1H), 7.51 (t, J=7.9 Hz, 1H), 7.44 (d, J=7.8 Hz, 1H), 7.23 (dd, J=9.1, 3.0 Hz, 1H), 7.19 (s, 1H), 3.20 (t, J=5.0 Hz, 4H), 2.67 (t, J=5.0 Hz, 4H), 2.53 (q, J=7.2 Hz, 2H), 1.17 (t, J=7.2 Hz, 3H). HRMS (ESI) m/z: $[M+H]^+$ calcd for $C_{22}H_{24}ClF_3N_7$, 478.1728; found, 478.1728.

Embodiment 46

Synthesis of Compound 46: 5-chloro-$N^2$-(5-(4-propylpiperazin-1-yl)pyridin-2-yl)-$N^4$-(3-(trifluoromethyl)phenyl)pyrimidine-2,4-diamine (46)

Experimental steps are the same as those of Embodiment 1, except that the intermediate III-1 is replaced by an intermediate III-7. White solid (yield: 54%). mp 192-195° C.; $^1$H NMR (400 MHz, Chloroform-d) δ 8.27 (s, 1H), 8.20 (s, 1H), 8.04 (s, 1H), 8.01 (d, J=9.1 Hz, 1H), 7.95 (s, 1H), 7.78 (d, J=8.1 Hz, 1H), 7.51 (t, J=7.9 Hz, 1H), 7.44 (d, J=7.8 Hz, 1H), 7.23 (dd, J=9.1, 3.0 Hz, 1H), 7.19 (s, 1H), 3.22-3.15 (m, 4H), 2.69-2.62 (m, 4H), 2.44-2.36 (m, 2H), 1.58 (m, 2H), 0.96 (t, J=7.4 Hz, 3H). HRMS (ESI) m/z: $[M+H]^+$ calcd for $C_{22}H_{24}ClF_3N_7$, 492.1885; found, 492.1886.

Embodiment 47

Synthesis of Compound 47: 5-chloro-$N^2$-(5-(4-(cyclopropylpiperazin-1-yl)pyridin-2-yl)-$N^4$-(3-(trifluoromethyl)phenyl)pyrimidine-2,4-diamine (47)

Experimental steps are the same as those of Embodiment 1, except that the intermediate III-1 is replaced by an intermediate III-8. White solid (yield: 54%). mp 207-209° C.; $^1$H NMR (400 MHz, Chloroform-d) δ 8.20 (s, 1H), 8.04 (t, J=2.5 Hz, 1H), 8.01 (d, J=9.1 Hz, 1H), 7.95 (s, 1H), 7.78 (d, J=8.3 Hz, 1H), 7.51 (t, J=7.9 Hz, 1H), 7.44 (d, J=7.8 Hz, 1H), 7.22 (dd, J=9.1, 3.0 Hz, 1H), 7.18 (s, 1H), 3.17-3.10 (m, 4H), 2.85-2.78 (m, 4H), 1.71 (m, 2H), 0.57-0.44 (m, 4H). HRMS (ESI) m/z: $[M+H]^+$ calcd for $C_{23}H_{24}ClF_3N_7$, 490.1728; found, 490.1730.

Embodiment 48

Synthesis of Compound 48: $N^2$-(5-(4-butylpiperazin-1-yl)pyridin-2-yl)-5-chloro-$N^4$-(3-(trifluoromethyl)phenyl)pyrimidine-2,4-diamine (48)

Experimental steps are the same as those of Embodiment 1, except that the intermediate III-1 is replaced by an intermediate III-9. White solid (yield: 54%). mp 167-170° C.; $^1$H NMR (400 MHz, Chloroform-d) δ 8.35 (s, 1H), 8.20 (d, J=3.0 Hz, 1H), 8.06-8.03 (m, 1H), 8.01 (d, J=9.1 Hz, 1H), 7.95 (s, 1H), 7.78 (d, J=8.1 Hz, 1H), 7.51 (t, J=7.9 Hz, 1H), 7.44 (d, J=7.8 Hz, 1H), 7.23 (dd, J=9.2, 3.2 Hz, 1H), 7.18 (s, 1H), 3.18 (t, J=5.0 Hz, 4H), 2.68-2.61 (m, 4H), 2.47-2.39 (m, 2H), 1.54 (tt, J=7.8, 6.1 Hz, 2H), 1.38 (h, J=7.4 Hz, 2H), 0.97 (t, J=7.3 Hz, 3H). HRMS (ESI) m/z: $[M+H]^+$ calcd for $C_{24}H_{28}ClF_3N_7$, 506.2041; found, 506.2041.

Embodiment 49

Synthesis of Compound 49: 1-(4-(6-((5-chloro-4-((3-(trifluoromethyl)phenyl)amino)pyrimidin-2-yl)amino]pyridin-3-yl)piperazine-1-yl)ethyl ketone (49)

Experimental steps are the same as those of Embodiment 1, except that the intermediate III-1 is replaced by an intermediate III-10. White solid (yield: 62%). mp 247-248°

C.; $^{1}$H NMR (400 MHz, DMSO-$d_6$) δ 9.57 (s, 1H), 9.14 (s, 1H), 8.28 (d, J=8.2 Hz, 1H), 8.23 (s, 1H), 8.04-7.98 (m, 2H), 7.80 (d, J=9.1 Hz, 1H), 7.58 (t, J=8.0 Hz, 1H), 7.45 (d, J=7.8 Hz, 1H), 7.26 (dd, J=9.1, 3.0 Hz, 1H), 3.59 (t, J=4.9 Hz, 4H), 3.10 (d, J=10.2 Hz, 2H), 3.04 (t, J=5.2 Hz, 2H), 2.05 (s, 3H). HRMS (ESI) m/z: $[M+H]^+$ calcd for $C_{22}H_{22}ClF_3N_7O$, 492.1521; found, 4921525.

Embodiment 50

Synthesis of Compound 50: 1-(4-(6-((5-chloro-4-((3-(trifluoromethyl)phenyl)amino)pyrimidin-2-yl)amino)pyridin-3-yl)piperazine-1-yl)propyl-1 (50)

Experimental steps are the same as those of Embodiment 1, except that the intermediate III-1 is replaced by an intermediate III-11. White solid (yield: 54%). mp 241-242° C.; $^{1}$H NMR (400 MHz, DMSO-$d_6$) δ 9.58 (s, 1H), 9.14 (s, 1H), 8.29 (d, J=8.3 Hz, 1H), 8.23 (s, 1H), 8.04-7.98 (m, 2H), 7.79 (d, J=9.0 Hz, 1H), 7.58 (t, J=8.0 Hz, 1H), 7.45 (d, J=7.9 Hz, 1H), 7.27 (dd, J=9.2, 3.0 Hz, 1H), 3.62-3.57 (m, 4H), 3.06 (dt, J=21.0, 5.1 Hz, 4H), 2.37 (q, J=7.4 Hz, 2H), 1.01 (t, J=7.4 Hz, 3H). HRMS (ESI) m/z: $[M+H]^+$ calcd for $C_{23}H_{24}ClF_3N_7O$, 506.1677; found, 506.1677.

Embodiment 51

Synthesis of Compound 51: 4-(6-((5-(4-chloro-4-((3-(trifluoromethyl)phenyl)amino)pyrimidin-2-yl)amino)pyridin-3-yl)piperazine-1-tert-butyl formate (51)

Experimental steps are the same as those of Embodiment 1, except that the intermediate III-1 is replaced by an intermediate III-12. White solid (yield: 64%). mp 233-234° C.; $^{1}$H NMR (400 MHz, Chloroform-d) δ 8.18 (s, 1H), 8.11 (s, 1H), 8.03-7.99 (m, 2H), 7.95 (s, 1H), 7.74 (d, J=8.0 Hz, 1H), 7.50 (t, J=7.9 Hz, 1H), 7.43 (d, J=7.8 Hz, 1H), 7.21 (dd, J=9.2, 2.9 Hz, 1H), 7.18 (s, 1H), 3.71-3.42 (m, 4H), 3.20-2.87 (m, 4H), 1.49 (s, 9H). $^{13}$C NMR (151 MHz, Chloroform-d) δ 156.82, 155.47, 154.76, 145.67, 143.04, 138.37, 137.21, 131.47 (q, J=32.4 Hz), 129.52, 127.13, 124.77, 122.85 (q, J=272.5), 122.95, 121.00 (d, J=3.7 Hz), 118.36 (d, J=3.6 Hz), 113.09, 106.00, 54.90 (2C), 49.57 (2C). HRMS (ESI) m/z: $[M+H]^+$ calcd for $C_{25}H_{28}N_7ClF_3O_2$, 550.1940; found, 550.1943.

Embodiment 52

Synthesis of Compound 52: 5-chloro-$N^2$-(5-(piperidin-1-yl)pyridin-2-yl)-$N^4$-(3-(trifluoromethyl)phenyl)pyrimidine-2,4-diamine (52)

Experimental steps are the same as those of Embodiment 1, except that the intermediate III-1 is replaced by an intermediate III-13. White solid (yield: 50%). mp 158-160° C.; $^{1}$H NMR (400 MHz, Chloroform-d) δ 8.17 (s, 1H), 8.14 (s, 1H), 8.01 (d, J=2.8 Hz, 1H), 7.96 (d, J=9.1 Hz, 1H), 7.92 (s, 1H), 7.77 (d, J=8.1 Hz, 1H), 7.49 (t, J=7.9 Hz, 1H), 7.41 (d, J=7.8 Hz, 1H), 7.21 (dd, J=9.1, 3.0 Hz, 1H), 7.16 (s, 1H), 3.12-3.05 (m, 4H), 1.73 (m, 4H), 1.62-1.53 (m, 2H). HRMS (ESI) m/z: $[M+H]^+$ calcd for $C_{21}H_{21}ClF_3N_6$, 449.1463; found, 449.1465.

Embodiment 53

Synthesis of Compound 53: 5-chloro-$N^2$-(5-morpholinopyridin-2-yl)-$N^4$-(3-(trifluoromethyl)phenyl)pyrimidine-2,4-diamine (53)

Experimental steps are the same as those of Embodiment 1, except that the intermediate III-1 is replaced by an intermediate III-14. White solid (yield: 26%). mp 205-207° C.; $^{1}$H NMR (400 MHz, DMSO-$d_6$) δ 9.55 (s, 1H), 9.14 (s, 1H), 8.28 (d, J=7.9 Hz, 1H), 8.22 (s, 1H), 7.99 (s, 2H), 7.78 (d, J=9.0 Hz, 1H), 7.57 (t, J=8.0 Hz, 1H), 7.44 (d, J=7.7 Hz, 1H), 7.23 (dd, J=9.0, 2.7 Hz, 1H), 3.80-3.70 (m, 4H), 3.10-3.00 (m, 4H). HRMS (ESI) m/z: $[M+H]^+$ calcd for $C_{21}H_{21}ClF_3N_6$, 451.1255; found, 451.1253.

Embodiment 54

Synthesis of Compound 54: 5-chloro-$N^2$-(5-thiomorpholinopyridin-2-yl)-$N^4$-(3-(trifluoromethyl)phenyl)pyrimidine-2,4-diamine (54)

Experimental steps are the same as those of Embodiment 1, except that the intermediate III-1 is replaced by an intermediate III-15. White solid (yield: 75%). mp 149-150° C.; $^{1}$H NMR (400 MHz, Chloroform-d) δ 8.23-8.16 (m, 2H), 8.02 (t, J=5.7 Hz, 2H), 7.97 (s, 1H), 7.76 (d, J=8.0 Hz, 1H), 7.52 (t, J=7.9 Hz, 1H), 7.45 (d, J=7.8 Hz, 1H), 7.28 (s, 1H), 7.23-7.18 (m, 1H), 3.49-3.40 (m, 4H), 2.84-2.77 (m, 4H). HRMS (ESI) m/z: $[M+H]^+$ calcd for $C_{20}H_{19}ClF_3N_6S$, 467.1027; found, 467.1027.

Embodiment 55

Synthesis of Compound 55: $N^2$-(5-(4-aminopiperidin-1-yl)pyridin-2-yl)-5-chloro-$N^4$-(3-(trifluoromethyl)phenyl)pyrimidine-2,4-diamine (55)

Experimental steps are the same as those of Embodiment 1, except that the intermediate III-1 is replaced by an intermediate III-16. White solid (yield: 58%). mp 191-192° C.; $^{1}$H NMR (400 MHz, DMSO-$d_6$) δ 9.53 (s, 1H), 9.13 (s, 1H), 8.29 (d, J=9.1 Hz, 1H), 8.22 (s, 1H), 8.00 (s, 1H), 7.98 (d, J=3.0 Hz, 1H), 7.76 (d, J=9.0 Hz, 1H), 7.58 (t, J=8.0 Hz, 1H), 7.44 (d, J=7.8 Hz, 1H), 7.23 (dd, J=9.1, 3.0 Hz, 1H), 6.89 (d, J=7.8 Hz, 1H), 3.54 (d, J=12.5 Hz, 2H), 2.74-2.64 (m, 2H), 1.81 (d, J=12.6 Hz, 2H), 1.49 (m, 2H), 1.39 (s, 9H), 1.28-1.14 (m, 1H). HRMS (ESI) m/z: $[M+H]^+$ calcd for $C_{21}H_{22}ClF_3N_7$, 464.1572; found, 464.1574.

Embodiment 56

Synthesis of Compound 56: 5-chloro-$N^2$-(5-(4-(dimethylamino)piperidin-1-yl)pyridin-2-yl)-$N^4$-(3-(trifluoromethyl)phenyl)pyrimidine-2, 4-diamine (56)

Experimental steps are the same as those of Embodiment 1, except that the intermediate III-1 is replaced by an intermediate III-17. White solid (yield: 62%). mp 196-197° C.; $^{1}$H NMR (400 MHz, Chloroform-d) δ 8.19 (s, 1H), 8.03 (d, J=3.0 Hz, 2H), 8.00 (d, J=9.1 Hz, 1H), 7.96 (s, 1H), 7.77 (d, J=8.0 Hz, 1H), 7.52 (t, J=7.9 Hz, 1H), 7.44 (d, J=7.8 Hz, 1H), 7.24 (dd, J=9.1, 3.0 Hz, 1H), 7.19 (s, 1H), 3.64 (d, J=12.7 Hz, 2H), 2.74 (t, J=10.9 Hz, 2H), 2.42 (s, 6H), 2.03 (d, J=12.7 Hz, 2H), 1.74 (m, 2H), 1.38-1.19 (m, 1H). $^{13}$C NMR (101 MHz, Chloroform-d) δ 156.92, 155.45, 154.78, 145.61, 143.15, 138.44, 137.07, 131.57 (q, J=32.4 Hz), 129.49, 126.86, 125.25, 123.95 (q, J=272.5), 122.54, 120.90 (d, J=3.6 Hz), 118.30 (d, J=3.6 Hz), 113.06, 105.41, 62.02 (2C), 49.72 (2C), 41.39 (2C), 27.92. HRMS (ESI) m/z: $[M+H]^+$ calcd for $C_{23}H_{26}ClF_3N_7$, 492.1885; found, 492.1886.

Embodiment 57

Synthesis of Compound 57: 1-(6-((5-chloro-4-((3-(trifluoromethyl)phenyl)amino)pyrimidin-2-yl)amino)pyridin-3-yl)piperidine-4-carbonitrile (57)

Experimental steps are the same as those of Embodiment 1, except that the intermediate III-1 is replaced by an intermediate III-18. White solid (yield: 53%). mp 202-203° C.; $^1H$ NMR (400 MHz, DMSO-$d_6$) δ 9.54 (s, 1H), 9.13 (s, 1H), 8.27 (d, J=7.7 Hz, 1H), 8.23 (s, 1H), 8.01 (d, J=3.2 Hz, 2H), 7.78 (d, J=9.1 Hz, 1H), 7.58 (t, J=8.0 Hz, 1H), 7.45 (d, J=7.8 Hz, 1H), 7.25 (dd, J=9.1, 3.1 Hz, 1H), 3.28 (m, 2H), 3.08-2.94 (m, 2H), 3.02 (m, 1H), 2.97 (m, 2H), 1.84 (m, 2H). HRMS (ESI) m/z: $[M+H]^+$ calcd for $C_{22}H_{20}ClF_3N_7$, 474.1415; found, 474.1419.

Embodiment 58

Synthesis of Compound 58: 5-chloro-$N^2$-(5-phenylpyridin-2-yl)-$N^4$-(3-(trifluoromethyl)phenyl)pyrimidine-2,4-diamine (58)

Experimental steps are the same as those of Embodiment 1, except that the intermediate III-1 is replaced by an intermediate III-19. White solid (yield: 58%). mp 210-211° C.; $^1H$ NMR (400 MHz, DMSO-$d_6$) δ 9.98 (s, 1H), 9.24 (s, 1H), 8.61 (d, J=2.6 Hz, 1H), 8.31 (s, 2H), 8.09-8.01 (m, 2H), 7.86 (dd, J=8.8, 2.5 Hz, 1H), 7.67 (d, J=7.0 Hz, 2H), 7.63 (t, J=7.9 Hz, 1H), 7.48 (t, J=7.5 Hz, 3H), 7.37 (t, J=7.3 Hz, 1H). HRMS (ESI) m/z: $[M+H]^+$ calcd for $C_{22}H_{16}ClF_3N_5$, 442.1041; found, 442.1045.

Embodiment 59

Synthesis of Compound 59: $N^2$-(5-(4-aminophenyl)pyridin-2-yl)-5-chloro-$N^4$-(3-(trifluoromethyl)phenyl)pyrimidine-2,4-diamine (59)

Experimental steps are the same as those of Embodiment 1, except that the intermediate III-1 is replaced by an intermediate III-20. White solid (yield: 41%). mp 206-207° C.; $^1H$ NMR (400 MHz, DMSO-$d_6$) δ 9.79 (s, 1H), 9.21 (s, 1H), 8.47 (s, 1H), 8.30 (d, J=11.9 Hz, 2H), 8.03 (s, 1H), 7.96 (d, J=8.7 Hz, 1H), 7.72 (d, J=8.5 Hz, 1H), 7.62 (t, J=8.0 Hz, 1H), 7.48 (d, J=7.7 Hz, 1H), 7.35 (d, J=8.3 Hz, 2H), 6.66 (d, J=8.1 Hz, 2H) 5.28 (s, 2H). HRMS (ESI) m/z: $[M+H]^+$ calcd for $C_{22}H_{17}ClF_3N_6$, 457.1150; found, 457.1149.

Embodiment 60

Synthesis of Compound 60: 5-chloro-$N^2$-(5-(1-(1-methyl-1H-pyrazol-4-yl)pyridin-2-yl)-$N^4$-(3-(trifluoromethyl)phenyl)pyrimidine-2,4-diamine (60)

Experimental steps are the same as those of Embodiment 1, except that the intermediate III-1 is replaced by an intermediate III-21. White solid (yield: 53%). mp 233-234° C.; $^1H$ NMR (400 MHz, DMSO-$d_6$) δ 9.88 (s, 1H), 9.24 (s, 1H), 8.52 (s, 1H), 8.30 (d, J=7.3 Hz, 2H), 8.03 (s, 1H), 7.96 (d, J=8.7 Hz, 1H), 7.79 (d, J=8.7 Hz, 1H), 7.62 (t, J=8.0 Hz, 1H), 7.49 (t, J=8.7 Hz, 3H), 6.81 (d, J=8.5 Hz, 2H), 2.94 (s, 6H). HRMS (ESI) m/z: $[M+H]^+$ calcd for $C_{24}H_{21}ClF_3N_6$, 485.1463; found, 485.1463.

Embodiment 61

Synthesis of Compound 61: 5-chloro-$N^2$-(5-(4-(dimethylamino)phenyl)pyridin-2-yl)-$N^4$-(3-(trifluoromethyl)phenyl)pyrimidine-2,4-diamine (61)

Experimental steps are the same as those of Embodiment 1, except that the intermediate III-1 is replaced by an intermediate III-22. White solid (yield: 36%). mp 265-266° C.; $^1H$ NMR (400 MHz, Chloroform-d) δ 8.97 (s, 1H), 8.36 (s, 1H), 7.66 (d, J=2.5 Hz, 1H), 7.47 (d, J=8.2 Hz, 1H), 7.43 (s, 1H), 7.28 (s, 1H), 7.16 (s, 1H), 7.09 (d, J=8.7 Hz, 1H), 7.01 (s, 1H), 6.88 (dd, J=8.7, 2.5 Hz, 1H), 6.75 (t, J=8.0 Hz, 1H), 6.61 (d, J=7.7 Hz, 1H), 3.02 (s, 3H). HRMS (ESI) m/z: $[M+H]^+$ calcd for $C_{20}H_{16}ClF_3N_7$, 446.1102; found, 446.1105.

Embodiment 62

Synthesis of Compound 62: 5-chloro-$N^2$-(5-(3,5-dimethylisoxazol-4-yl)pyridin-2-yl)-$N^4$-(3-(trifluoromethyl)phenyl)pyrimidine-2, 4-diamine (62)

Experimental steps are the same as those of Embodiment 1, except that the intermediate III-1 is replaced by an intermediate III-23. White solid (yield: 27%). mp 204-205° C.; $^1H$ NMR (400 MHz, DMSO-$d_6$) δ 9.99 (s, 1H), 9.26 (s, 1H), 8.33-8.26 (m, 3H), 8.07-8.00 (m, 2H), 7.64-7.55 (m, 2H), 7.47 (d, J=7.8 Hz, 1H), 2.40 (s, 3H), 2.22 (s, 3H). HRMS (ESI) m/z: $[M+H]^+$ calcd for $C_{21}H_{17}ClF_3N_6O$, 461.1099; found, 461.1099.

Embodiment 63

Synthesis of Compound 63: 5-chloro-$N^2$-(5-(furan-3-yl)pyridin-2-yl)-$N^4$-(3-(trifluoromethyl)phenyl)pyrimidine-2,4-diamine (63)

Experimental steps are the same as those of Embodiment 1, except that the intermediate III-1 is replaced by an intermediate III-24. White solid (yield: 58%). mp 198-199° C.; $^1H$ NMR (400 MHz, DMSO-$d_6$) δ 9.88 (s, 1H), 9.21 (s, 1H), 8.56 (s, 1H), 8.33 (d, J=8.1 Hz, 1H), 8.29 (s, 1H), 8.18 (s, 1H), 8.01 (s, 1H), 7.98 (d, J=8.7 Hz, 1H), 7.79 (dd, J=8.7, 2.5 Hz, 1H), 7.76 (s, 1H), 7.61 (t, J=8.0 Hz, 1H), 7.46 (d, J=7.9 Hz, 1H), 6.97 (s, 1H). HRMS (ESI) m/z: $[M+H]^+$ calcd for $C_{20}H_{14}ClF_3N_5O$, 432.0833; found, 432.0834.

Embodiment 64

Synthesis of Compound 64: 5-chloro-$N^2$-(5-(thiophen-3-yl)pyridin-2-yl)-$N^4$-(3-(trifluoromethyl)phenyl)pyrimidine-2,4-diamine (64)

Experimental steps are the same as those of Embodiment 1, except that the intermediate III-1 is replaced by an intermediate III-25. White solid (yield: 42%). mp 221-222° C.; $^1H$ NMR (400 MHz, DMSO-$d_6$) δ 9.91 (s, 1H), 9.23 (s, 1H), 8.66 (s, 1H), 8.34-8.27 (m, 2H), 8.01 (d, J=10.3 Hz, 2H), 7.89 (d, J=14.7 Hz, 2H), 7.69-7.56 (m, 3H), 7.47 (d, J=7.5 Hz, 1H). $^{13}C$ NMR (101 MHz, DMSO-$d_6$) δ 157.11, 156.14, 155.50, 152.20, 145.73, 139.96, 138.78, 135.30, 130.11, 129.80 (d, J=32.4 Hz), 127.79, 126.88, 126.21, 125.33, 123.29 (q, J=272.5), 120.72, 120.47 (d, J=3.6 Hz), 119.20 (d, J=3.6 Hz), 113.08, 105.94. HRMS (ESI) m/z: $[M+H]^+$ calcd for $C_{20}H_{14}ClF_3N_5S$, 448.0605; found, 448.0609.

Embodiment 65

Synthesis of Compound 65: 5-fluoro-$N^2$-(5-(4-methylpiperazin-1-yl)pyridin-2-yl)-$N^4$-(3-(trifluoromethyl)phenyl)pyrimidine-2,4-diamine (65)

Experimental steps are the same as those of Embodiment 1, except that the intermediate I-1 is replaced by an intermediate I-3. White solid (yield: 43%). mp 181-182° C.; $^1H$ NMR (400 MHz, DMSO-$d_6$) δ 9.66 (d, J=1.8 Hz, 1H), 9.39 (s, 1H), 8.39 (dd, J=8.3, 2.2 Hz, 1H), 8.19 (d, J=3.6 Hz, 1H), 8.07 (d, J=2.0 Hz, 1H), 7.99 (d, J=3.0 Hz, 1H), 7.87 (d, J=9.1 Hz, 1H), 7.55 (t, J=8.0 Hz, 1H), 7.39 (dd, J=8.0, 1.6 Hz, 1H), 7.30 (dd, J=9.1, 3.1 Hz, 1H), 3.13-3.07 (m, 4H), 2.51 (dd, J=3.8, 1.9 Hz, 4H), 2.25 (s, 3H). HRMS (ESI) m/z: $[M+H]^+$ calcd for $C_{21}H_{22}F_4N_7$, 448.1867; found, 448.1868.

Embodiment 66

Synthesis of Compound 66: 5-methyl-$N^2$-(5-(4-methylpiperazin-1-yl)pyridin-2-yl)-$N^4$-(3-(trifluoromethyl)phenyl)pyrimidine-2,4-diamine (66)

Experimental steps are the same as those of Embodiment 1, except that the intermediate I-1 is replaced by an intermediate I-4. White solid (yield: 43%). mp 204-205° C.; $^1H$ NMR (400 MHz, DMSO-$d_6$) δ 9.09 (s, 1H), 8.59 (s, 1H), 8.34 (dd, J=8.3, 2.2 Hz, 1H), 7.99 (s, 1H), 8.00-7.95 (m, 2H), 7.93 (d, J=9.1 Hz, 1H), 7.55 (t, J=8.0 Hz, 1H), 7.36 (d, J=7.5 Hz, 1H), 7.25 (dd, J=9.2, 3.0 Hz, 1H), 3.09 (t, J=5.0 Hz, 4H), 2.56-2.48 (m, 4H), 2.27 (s, 3H), 2.14 (s, 3H). HRMS (ESI) m/z: $[M+H]^+$ calcd for $C_{22}H_{25}F_3N_7$, 444.2118; found, 444.2121.

Embodiment 67

Synthesis of Compound 67: 5-methyl-$N^2$-(5-(4-methoxypiperazin-1-yl)pyridin-2-yl)-$N^4$-(3-(trifluoromethyl)phenyl)pyrimidine-2,4-diamine (67)

Experimental steps are the same as those of Embodiment 1, except that the intermediate I-1 is replaced by an intermediate I-5. White solid (yield: 42%). mp 192-193° C.; $^1H$ NMR (400 MHz, DMSO-$d_6$) δ 9.12 (s, 1H), 9.09 (s, 1H), 8.47 (dd, J=8.2, 2.2 Hz, 1H), 8.14 (s, 1H), 8.01-7.94 (m, 2H), 7.93 (s, 1H), 7.52 (t, J=8.0 Hz, 1H), 7.38-7.30 (m, 1H), 7.30 (dd, J=9.1, 3.1 Hz, 1H), 3.88 (s, 3H), 3.07 (t, J=5.0 Hz, 4H), 2.46 (t, J=5.0 Hz, 4H), 2.22 (s, 3H). HRMS (ESI) m/z: $[M+H]^+$ calcd for $C_{22}H_{25}F_3N_7O$, 460.2067; found, 460.2062.

Embodiment 68

Synthesis of Compound 68: $N^2$-(5-(thiophen-3-yl)pyridin-2-yl)-$N^4$-(3-(trifluoromethyl)phenyl)pyrimidine-2,4-diamine (68)

Experimental steps are the same as those of Embodiment 1, except that the intermediate I-1 is replaced by an intermediate I-2 and the intermediate III-1 is replaced by an intermediate III-25. White solid (yield: 63%). mp 222-223° C.; $^1H$ NMR (400 MHz, DMSO-$d_6$) δ 9.82 (d, J=7.7 Hz, 2H), 8.72-8.67 (m, 1H), 8.32-8.26 (m, 1H), 8.24 (d, J=8.8 Hz, 1H), 8.19 (d, J=5.7 Hz, 1H), 8.01 (dd, J=8.8, 2.5 Hz, 1H), 7.95 (d, J=2.1 Hz, 1H), 7.87 (dd, J=3.0, 1.3 Hz, 1H), 7.67 (dd, J=5.0, 2.9 Hz, 1H), 7.66-7.50 (m, 2H), 7.37-7.31 (m, 1H), 6.38 (d, J=5.7 Hz, 1H). RMS (ESI) m/z: $[M+H]^+$ calcd for $C_{20}H_{15}F_3N_5S$, 414.0995; found, 414.0998.

Embodiment 69

Synthesis of Compound 69: 5-fluoro-$N^2$-(5-(thiophen-3-yl)pyridin-2-yl)-$N^4$-(3-(trifluoromethyl)phenyl)pyrimidine-2,4-diamine (69)

Experimental steps are the same as those of Embodiment 1, except that the intermediate I-1 is replaced by an intermediate I-3 and the intermediate III-1 is replaced by an intermediate III-25. White solid (yield: 60%). mp 225-226° C.; $^1H$ NMR (400 MHz, DMSO-$d_6$) δ 9.88 (s, 1H), 9.79 (s, 1H), 8.67 (d, J=2.4 Hz, 1H), 8.46 (dd, J=8.3, 2.2 Hz, 1H), 8.27 (d, J=3.5 Hz, 1H), 8.10 (d, J=9.0 Hz, 2H), 7.99 (dd, J=8.8, 2.5 Hz, 1H), 7.87 (dd, J=3.0, 1.4 Hz, 1H), 7.67 (m, 1H), 7.61-7.53 (m, 2H), 7.42 (dd, J=7.6, 1.6 Hz, 1H). HRMS (ESI) m/z: $[M+H]^+$ calcd for $C_{20}H_{14}F_4N_5S$, 432.0901; found, 432.0902.

Embodiment 70

Synthesis of Compound 70: 5-methyl-$N^2$-(5-(thiophen-3-yl)pyridin-2-yl)-$N^4$-(3-(trifluoromethyl)phenyl)pyrimidine-2,4-diamine (70)

Experimental steps are the same as those of Embodiment 1, except that the intermediate I-1 is replaced by an intermediate I-4 and the intermediate III-1 is replaced by an intermediate III-25. White solid (yield: 60%). mp 198-199° C.; $^1H$ NMR (400 MHz, DMSO-$d_6$) δ 9.60 (s, 1H), 8.74 (s, 1H), 8.65 (d, J=2.5 Hz, 1H), 8.39 (dd, J=8.2, 2.1 Hz, 1H), 8.11 (d, J=8.8 Hz, 1H), 8.05 (s, 1H), 8.00 (s, 1H), 7.94 (dd, J=8.8, 2.5 Hz, 1H), 7.86 (dd, J=2.9, 1.4 Hz, 1H), 7.67 (dd, J=5.0, 3.0 Hz, 1H), 7.63-7.55 (m, 2H), 7.41 (d, J=8.6 Hz, 1H), 2.18 (s, 3H). HRMS (ESI) m/z: $[M+H]^+$ calcd for $C_{21}H_{17}F_3N_5S$, 428.1151; found, 428.1153.

Embodiment 71

Synthesis of Compound 71: 5-methoxy-$N^2$-(5-(thiophen-3-yl)pyridin-2-yl)-$N^4$-(3-(trifluoromethyl)phenyl)pyrimidine-2,4-diamine (71)

Experimental steps are the same as those of Embodiment 1, except that the intermediate I-1 is replaced by an intermediate I-5 and the intermediate III-1 is replaced by an intermediate III-25. White solid (yield: 58%). mp 202-203° C.; $^1H$ NMR (400 MHz, DMSO-$d_6$) δ 9.58 (s, 1H), 9.21 (s, 1H), 8.66 (dd, J=2.5, 0.8 Hz, 1H), 8.53 (dd, J=8.8, 1.9 Hz, 1H), 8.24-8.18 (m, 1H), 8.16 (s, 1H), 8.00 (s, 1H), 7.97 (dd, J=8.8, 2.6 Hz, 1H), 7.84 (dd, J=2.9, 1.4 Hz, 1H), 7.66 (dd, J=5.0, 2.9 Hz, 1H), 7.62-7.51 (m, 2H), 7.36 (d, J=7.5 Hz, 1H), 3.92 (s, 3H). HRMS (ESI) m/z: $[M+H]^+$ calcd for $C_{21}H_{17}F_3N_5OS$, 444.1100; found, 4644.1103.

Embodiment 72

Evaluation of in vitro inhibitory effect on cathepsin C:

The inhibitory effect of the compound on human recombinant cathepsin C was determined in a black 384-well plate.

Human recombinant cathepsin C was diluted to a concentration of 5 nM in an assay buffer containing 25 mM N-2-hydroxyethylpiperazine-N'-2-ethanesulfonic acid (HEPES) buffer, 50 mM NaCl, 5 mM MDTT, and 0.01% (v/v) Tritonx-100 (pH 5.0). 20 μL of the diluted enzyme (corresponding to 2 nM cathepsin C in the determination) and 10 μL of the compound to be tested or positive control (AZD7986) were added to the wells, followed by incubating at 25° C. for 30 min and then adding 20 μL of substrate (h-gly-arg-amc) to reach a final concentration of 100 μM. After reacting for 60 min, the absorbance of AMC was measured at EXX 350 nm and EM, 450 nm. The above test results were calculated by SPSS17.0 to obtain $IC_{50}$ value, and the results are shown in the table below:

Embodiment 73

Evaluation of In Vitro Inhibitory Effect on Intracellular Cathepsin C:

The intracellular enzyme activity assay was performed in a 96-well plate. 30 μL of PBS cell suspension containing U937 or THP-1 cells was added to the wells such that each well contained $3\times10^5$ cells, and 10 μL of AZD7986 or the compound to be tested was added to the wells. After incubation at 37° C. for 1 h, h-gly-arg-amc (200 μM) was added and the reaction started. The incubation was continued at 37° C. for 1 h, and the absorbance of AMC was measured at EXX 350 nm and EM, 450 nm. The above test results were calculated by SPSS17.0 to obtain $IC_{50}$ value, and the results are shown in the table below:

| NO. | CatC $IC_{50}$ (nM) | THP-1 CatC $IC_{50}$ (nM) | U937 CatC $IC_{50}$ (nM) |
|---|---|---|---|
| 1 | 984.6 ± 3.9 | 1055.1 ± 3.7 | 1660.4 ± 5.9 |
| 2 | NT | NT | NT |
| 3 | NT | NT | NT |
| 4 | NT | NT | NT |
| 5 | NT | NT | NT |
| 6 | NT | NT | NT |
| 7 | NT | NT | NT |
| 8 | NT | NT | NT |
| 9 | 678.5 ± 1.40 | 1008.2 ± 1.06 | 985.2 ± 2.41 |
| 10 | NT | NT | NT |
| 11 | >5000 | >3000 | NT |
| 12 | 2081.5 | >3000 | NT |
| 13 | 1307.2 ± 4.3 | >3000 | NT |
| 14 | NT | NT | NT |
| 15 | NT | NT | NT |
| 16 | 2625.4 | >3000 | NT |
| 17 | NT | NT | NT |
| 18 | 2022.1 | >3000 | NT |
| 19 | NT | NT | NT |
| 20 | NT | NT | NT |
| 21 | NT | NT | NT |
| 22 | NT | NT | NT |
| 23 | NT | NT | NT |
| 24 | 785.3 ± 2.71 | 993.5 ± 5.17 | 1225.4 ± 3.02 |
| 25 | NT | NT | NT |
| 26 | NT | NT | NT |
| 27 | NT | NT | NT |
| 28 | NT | NT | NT |
| 29 | NT | NT | NT |
| 30 | NT | NT | NT |
| 31 | NT | NT | NT |
| 32 | NT | NT | NT |
| 33 | NT | NT | NT |
| 34 | NT | NT | NT |
| 35 | 295.8 ± 1.20 | 203.5 ± 1.64 | 248.3 ± 0.85 |
| 36 | 416.9 ± 0.57 | 288.5 ± 0.70 | 512.5 ± 1.32 |
| 37 | 2989.3 | >3000 | NT |
| 38 | 1990.5 ± 3.63 | >3000 | NT |
| 39 | 1560.9 ± 4.11 | >3000 | 2086.4 |

-continued

| NO. | CatC $IC_{50}$ (nM) | THP-1 CatC $IC_{50}$ (nM) | U937 CatC $IC_{50}$ (nM) |
|---|---|---|---|
| 40 | 142.5 ± 0.90 | 82.5 ± 1.8 | 142.6 ± 2.7 |
| 41 | 57.4 ± 0.73 | 25.2 ± 0.90 | 23.6 ± 2.1 |
| 42 | 136.1 ± 1.2 | 75.8 ± 1.3 | 96.7 ± 3.9 |
| 43 | 207.2 ± 2.04 | 151.2 ± 1.76 | 324.8 ± 3.01 |
| 44 | 115.2 ± 1.35 | 117.9 ± 1.04 | 168.4 ± 2.77 |
| 45 | 58.2 ± 0.83 | 27.9 ± 1.02 | 41.5 ± 2.30 |
| 46 | 92.0 ± 0.98 | 73.6 ± 1.03 | 106.7 ± 1.5 |
| 47 | 981.6 ± 1.1 | 710.0 ± 1.8 | 1201.7 ± 2.6 |
| 48 | 202.3 ± 1.3 | 240.5 ± 1.2 | 198.5 ± 2.03 |
| 49 | 308.5 ± 0.67 | 655.9 ± 2.8 | 519.4 ± 4.0 |
| 50 | NT | NT | NT |
| 51 | 78.7 ± 1.01 | 52.3 ± 0.97 | 91.0 ± 1.20 |
| 52 | NT | NT | NT |
| 53 | NT | NT | NT |
| 54 | 407.6 ± 3.23 | NT | 1478.1 ± 6.02 |
| 55 | 86.5 ± 0.69 | 182.4 ± 2.1 | 355.6 ± 5.8 |
| 56 | 32.5 ± 1.10 | 40.2 ± 0.77 | 29.5 ± 1.30 |
| 57 | NT | NT | NT |
| 58 | 213.5 ± 2.00 | 287.5 ± 4.26 | 305.6 ± 4.2 |
| 59 | 158.2 ± 1.2 | 271.4 ± 1.64 | 257.7 ± 2.6 |
| 60 | 62.2 ± 0.8 | 109.5 ± 2.1 | 135.3 ± 2.8 |
| 61 | 305.3 ± 2.7 | 278.2 ± 1.2 | 377.5 ± 0.9 |
| 62 | NT | NT | NT |
| 63 | NT | NT | NT |
| 64 | 57.2 ± 0.77 | 42.3 ± 1.20 | 74.5 ± 0.98 |
| 65 | 90.3 ± 1.12 | 61.4 ± 0.80 | 88.6 ± 1.19 |
| 66 | 209.5 ± 1.29 | 169.5 ± 1.24 | 188.9 ± 1.01 |
| 67 | 166.9 ± 2.01 | 139.8 ± 1.03 | 156.5 ± 2.13 |
| 68 | 53.1 ± 1.43 | 89.0 ± 2.1 | 57.2 ± 1.20 |
| 69 | 66.2 ± 0.69 | 85.4 ± 1.42 | 77.0 ± 1.03 |
| 70 | 108.9 ± 0.89 | 83.2 ± 1.06 | 133.7 ± 1.22 |
| 71 | 133.4 ± 1.01 | 90.6 ± 1.13 | 149.2 ± 2.52 |

"NT": Not Tested, because no inhibitory effect of the compound on cathepsin C was detected at a concentration of 0.2 μM.

Embodiment 74

In Vivo Acute Toxicity Evaluation:

The compound 41 was preferably selected for in vivo activity test. 20 ICR mice (about half, about 20 g, purchased from the Department of Animal Science of Anhui Medical University) were selected and aged 6 to 8 weeks for the acute toxicity test of the compound 41. The mice were randomly divided into two groups and subjected to adaptive feeding for one week. After fasting for 12 h, the compound 41 was administered orally at 1500 mg/kg (0.5% CMC-Na as solvent) at one time. The body weight, mortality and behavior of the mice were observed and recorded daily for one week. Subsequently, the mice were anesthetized and the tissues were used for HE staining.

The acute toxicity test result was $LD_{50}$>1500 mg/kg, and no pathological changes were found in tissues and organs.

Embodiment 75

Test of In Vivo Inhibition of Cathepsin C and NSPs.

C57BL/6 mice (half sex, about 20 g, purchased from the Department of Animal Science of Anhui Medical University) were randomly divided into four groups (N=6). Mice in the group treated with the compound 41 were orally administered with the compound 1 at 5 mg/kg, 15 mg/kg, and 45 mg/kg daily for 6 days. Mice in the control group were administered with the same amount of normal saline twice a day for 6 days. At the end, bone marrow and blood were drawn to analyze the activity of cathepsin C and NSPs. Bone marrow and blood lysates were added to a 384-well plate. A synthetic peptide substrate was used to analyze the activity of NSPs and cathepsin C.

Figure 1B:
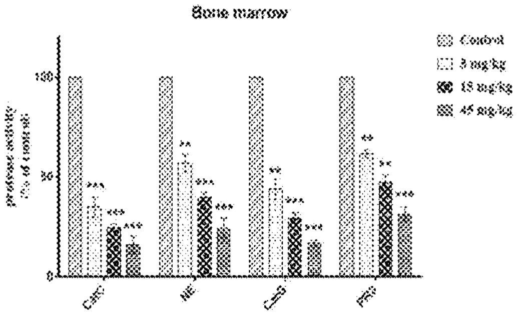
Figure 2A:
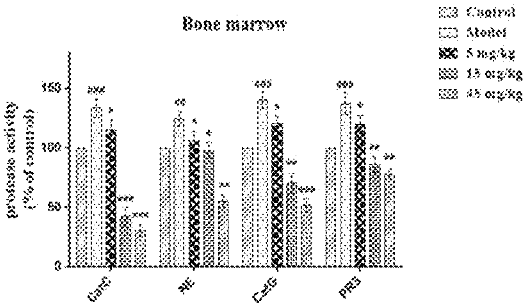
FIGS. 2A-2G show inhibitory effects of compound 41 of the present disclosure on cathepsin C and downstream NSPs in COPD model mice in a model group.
Figure 2B:
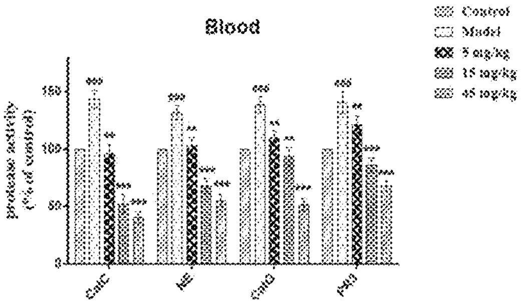
Figure 2C:
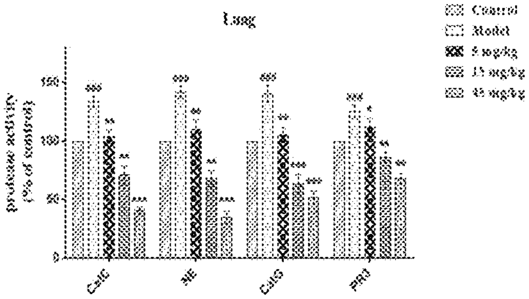
Figure 2D:
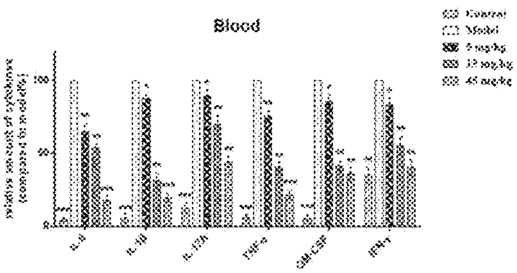
Figure 2E:
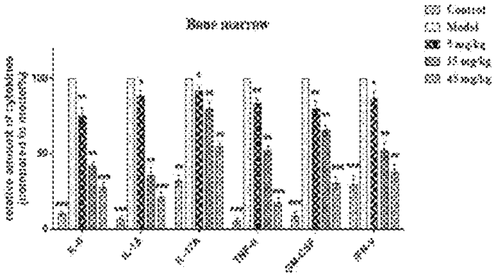
Figure 2F:
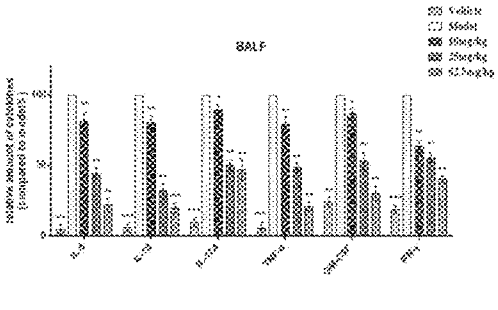
Figure 2G:
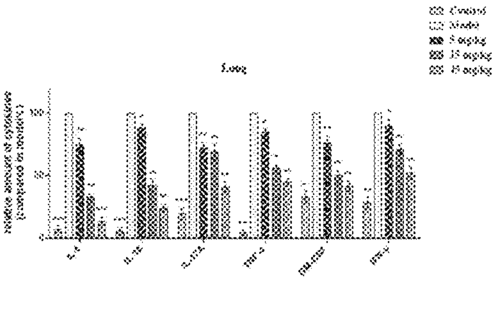
Figure 3A:
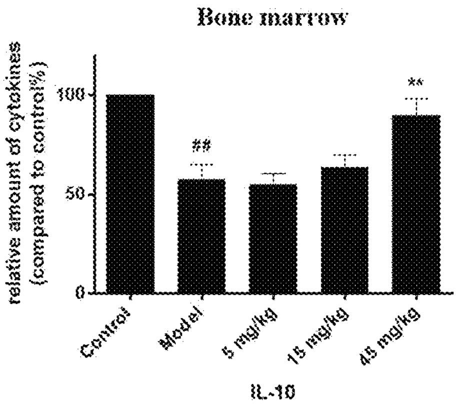
FIGS. 3A-3D show an effect of compound 41 of the present disclosure on inflammatory factors in COPD model mice.
Figure 3B:
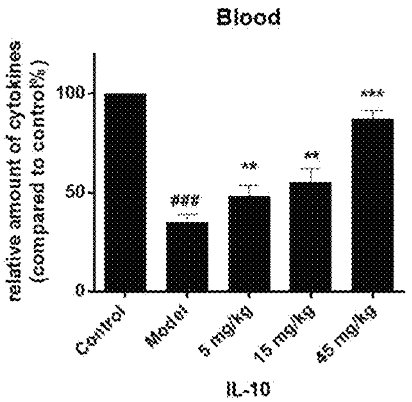
Figure 3C:
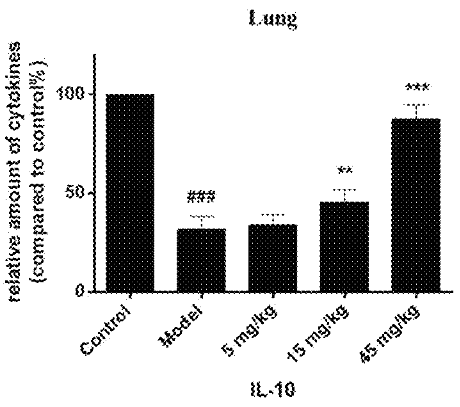
Figure 3D:
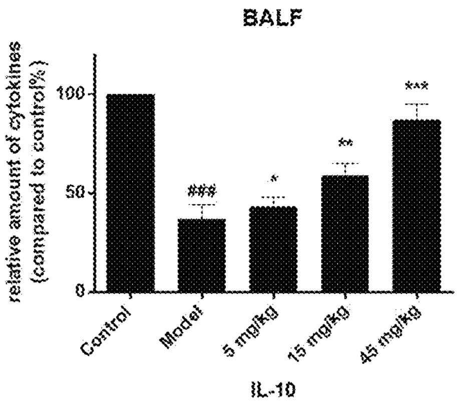

As shown in FIGS. 1A-1B, it is observed that dose-dependency of cathepsin C activity and downstream NSP activation is decreased obviously in both bone marrow and blood.

Embodiment 76

In Vivo Anti-Inflammatory Activity Assessment:

A combination of fumigation and LPS (Sigma) was used. Rats were orally administered with saline (control group and model group, N=8) or the compound 41 twice a day at doses of 5 mg/kg (N=8), 15 mg/kg (N=8), or 45 mg/kg (N=8), respectively, which lasted from day 1 to day 13 and day 15 to day 30 (28 days in total). Except for the negative control group, all rats were exposed to cigarette smoke (XIONG-SHI) for 45 min in each day from day 1 to day 13 and day 15 to day 30, subjected to tracheal instillation of LPS (200 g) on day 0 (start point of the study), and subjected to tracheal instillation of LPS (100 g) on day 14. The body weight was recorded every three days, and the behavior, coat color and breathing were observed daily. On day 31, the animals were euthanized with an overdose of chloral hydrate. Subsequently, lung, bronchoalveolar lavage fluid (BALF), blood, bone marrow samples were collected and stored at −80° C. until being detected. The levels of cathepsin C and NSP were detected with previously described methods, and cytokine levels in all samples were analyzed by ELISA kits (MULTI SCIENCES).

Compared with the normal group, the rats in the model group exhibited typical symptoms of COPD, including dyspnea, increased airway mucus, yellow coat, and loss of appetite, one week after the start of modeling. Compared with the model group, the COPD rats in the group treated with the compound 41 significantly less suffered from pulmonary inflammation and systemic inflammation. The rats in the group treated with the compound 41 lost their weight slowly and gained weight slightly after about 20 days. As shown in FIGS. 2A-2G, it is observed that dose-dependency of cathepsin C activity and downstream NSP activation is decreased obviously in bone marrow, blood, lung, and BALF.

To evaluate the histopathological changes in a COPD rat model after being treated with the compound 41, H&E staining was performed on lung tissue. In the model group, it was observed that there were obvious pro-inflammatory changes, including alveolar hemorrhage and dilation, partial alveolar fusion, inflammatory cell infiltration, and alveolar structure destruction. However, the compound 41 ameliorated these histopathological changes in an obvious dose-dependent manner. As shown in FIGS. 3A-3D, the rats in the model group exhibit an obvious inflammatory response, accompanied by significant upregulation of cytokine levels (IFN-γ, IL-1β, IL-6, IL-17, TNF-α, and GM-CSF) and downregulation of IL-10 levels in different tissues (bone marrow, blood, lung, and BALF). However, the rats in the group treated with the compound 41 show a decreased level of pro-inflammatory cytokines (IFN-γ, IL-1β, IL-6, IL-17, TNF-α, and GM-CSF), a reduced concentration of anti-inflammatory drugs, and increased cytokines (IL-10) in a dose-dependent manner.

The basic principles and main features as well as the advantages of the present disclosure have been shown and described above. Those skilled in the art should understand that the present disclosure is not limited by the above-mentioned embodiments. The above-mentioned embodiments and descriptions only illustrate the principles of the present disclosure. Without departing from the spirit and scope of the present disclosure, various changes and modifications may be made, which all fall within the scope of the present disclosure. The scope of the present disclosure is defined by the appended claims and their equivalents.

What is claimed is:

1. A method for regulating a catalytic activity of cathepsin in a subject in need thereof, comprising administering to the subject an effective amount of a pyrimidine-2,4-diamine compound as shown in Formula II:

Formula II

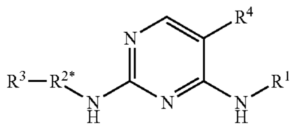

wherein, $R^1$ is selected from the group consisting of phenyl and substituted phenyl: $R^{2*}$ is one selected from the group consisting of pyridyl, pyrimidinyl, and pyridazinyl; $R^3$ is one selected from the group consisting of N-methylpiperazine, N-ethylpiperazine, N-propylpiperazine, N-cyclopropylpiperazine, N-butylpiperazine, and piperazine; $R^4$ is one selected from the group consisting of hydrogen, fluorine, chlorine, bromine, methyl, ethyl, and methoxy.

2. The method according to claim 1, wherein the cathepsin is cathepsin C.

* * * * *